United States Patent
Furst et al.

(10) Patent No.: US 7,803,181 B2
(45) Date of Patent: *Sep. 28, 2010

(54) OSTIAL STENT

(75) Inventors: Joseph G. Furst, Lyndhurst, OH (US); Ravish Sachar, Raleigh, NC (US)

(73) Assignee: Icon Interventional Systems, Inc., Cleveland, OH (US)

( * ) Notice: Subject to any disclaimer, the term of this patent is extended or adjusted under 35 U.S.C. 154(b) by 116 days.

This patent is subject to a terminal disclaimer.

(21) Appl. No.: 12/172,550

(22) Filed: Jul. 14, 2008

(65) Prior Publication Data

US 2008/0275541 A1 Nov. 6, 2008

Related U.S. Application Data

(63) Continuation of application No. 11/271,528, filed on Nov. 12, 2005, now Pat. No. 7,455,688.

(60) Provisional application No. 60/627,421, filed on Nov. 12, 2004, provisional application No. 60/658,289, filed on Mar. 3, 2005.

(51) Int. Cl.
*A61F 2/06* (2006.01)
(52) U.S. Cl. ..................................... 623/1.31
(58) Field of Classification Search ........ 623/1.11–1.48
See application file for complete search history.

(56) References Cited

U.S. PATENT DOCUMENTS

| | | | |
|---|---|---|---|
| 3,964,482 A | 6/1976 | Gerstel et al. |
| 4,886,062 A | 12/1989 | Wiktor |
| 4,913,141 A | 4/1990 | Hillstead |
| 4,994,071 A | 2/1991 | MacGregor |
| 5,019,085 A | 5/1991 | Hillstead |
| 5,147,370 A | 9/1992 | McNamara et al. |
| 5,263,349 A | 11/1993 | Felix et al. |
| 5,372,600 A | 12/1994 | Beyar et al. |
| 5,423,849 A | 6/1995 | Engelson et al. |
| 5,437,744 A | 8/1995 | Carlen |
| 5,456,712 A | 10/1995 | Maginot |
| 5,466,242 A | 11/1995 | Mori |
| 5,507,768 A | 4/1996 | Lau et al. |
| 5,549,635 A | 8/1996 | Solar |
| 5,556,754 A | 9/1996 | Singer |

(Continued)

FOREIGN PATENT DOCUMENTS

CA 2172187 6/2001

(Continued)

OTHER PUBLICATIONS

Matsuda, 2002. Device-directed therapeutic drug delivery systems. Journal of Controlled Release, vol. 78:125-131.

(Continued)

*Primary Examiner*—Suzette J Gherbi
(74) *Attorney, Agent, or Firm*—Fay Sharpe LLP; Brian E. Turung

(57) ABSTRACT

An improved medical device for use in the treatment of stenosis of the ostium of tubular organs, such as, but not limited to blood vessels. The improved medical device includes a configuration and design that enables at least one end region of the improved medical device to flare outwardly.

23 Claims, 4 Drawing Sheets

U.S. PATENT DOCUMENTS

| | | |
|---|---|---|
| 5,578,645 A | 11/1996 | Askanazi |
| 5,605,696 A | 2/1997 | Eury |
| 5,607,444 A | 3/1997 | Lam |
| 5,607,467 A | 3/1997 | Froix |
| 5,609,629 A | 3/1997 | Fearnot et al. |
| 5,632,760 A | 5/1997 | Sheiban et al. |
| 5,632,840 A | 5/1997 | Campbell |
| 5,643,278 A | 7/1997 | Wijay |
| 5,649,977 A | 7/1997 | Campbell |
| 5,669,932 A | 9/1997 | Fischell et al. |
| 5,843,172 A | 12/1998 | Yan |
| 5,868,777 A | 2/1999 | Lam |
| 6,093,520 A | 7/2000 | Vladimirsky |
| 6,096,071 A | 8/2000 | Yadav |
| 6,117,167 A | 9/2000 | Goicoechea et al. |
| 6,174,329 B1 | 1/2001 | Callol et al. |
| 6,174,330 B1 | 1/2001 | Stinson |
| 6,240,616 B1 | 6/2001 | Yan |
| 6,241,757 B1 | 6/2001 | An et al. |
| 6,293,964 B1 | 9/2001 | Yadav |
| 6,334,856 B1 | 1/2002 | Allen et al. |
| 6,365,616 B1 | 4/2002 | Kohn |
| 6,533,949 B1 | 3/2003 | Yeshurun |
| 6,558,361 B1 | 5/2003 | Yeshurun |
| 6,626,936 B2 | 9/2003 | Stinson |
| 6,790,372 B2 | 9/2004 | Roy et al. |
| 6,861,406 B2 | 3/2005 | Mascarenhas |
| 6,887,851 B2 | 5/2005 | Mascarenhas |
| 6,914,049 B2 | 7/2005 | Mascarenhas |
| 6,924,087 B2 | 8/2005 | Yeshurun et al. |
| 6,926,690 B2 | 8/2005 | Renati |
| 6,939,863 B2 | 9/2005 | Chen |
| 2001/0013166 A1 | 8/2001 | Yan |
| 2001/0053936 A1 | 12/2001 | Whitmore |
| 2002/0082679 A1 | 6/2002 | Sirhan et al. |
| 2002/0098278 A1 | 7/2002 | Bates |
| 2002/0111633 A1 | 8/2002 | Stoltze et al. |
| 2002/0142974 A1 | 10/2002 | Kohn |
| 2002/0155737 A1 | 10/2002 | Roy |
| 2002/0169498 A1 | 11/2002 | Kim et al. |
| 2003/0083734 A1 | 5/2003 | Friedrich et al. |
| 2003/0100499 A1 | 5/2003 | Epstein |
| 2003/0171708 A1 | 9/2003 | Segura et al. |
| 2004/0072105 A1 | 4/2004 | Yeshurun |
| 2004/0093058 A1 | 5/2004 | Cottone et al. |
| 2004/0093076 A1 | 5/2004 | White et al. |
| 2004/0093077 A1 | 5/2004 | White et al. |
| 2004/0098014 A1 | 5/2004 | Flugelman |
| 2004/0243225 A1 | 12/2004 | Ragheb |
| 2004/0254627 A1 | 12/2004 | Thompson et al. |
| 2005/0029223 A1 | 2/2005 | Yeshurun |
| 2005/0049678 A1 | 3/2005 | Cocks et al. |
| 2005/0154447 A1 | 7/2005 | Goshgarian |
| 2005/0165358 A1 | 7/2005 | Yeshurun |
| 2005/0209566 A1 | 9/2005 | Yeshurun |
| 2005/0222672 A1 | 10/2005 | Shmulewitz |
| 2006/0051404 A1 | 3/2006 | Yeshurun |
| 2007/0088425 A1 | 4/2007 | Schaeffer |

FOREIGN PATENT DOCUMENTS

| | | |
|---|---|---|
| EP | 734721 | 2/1996 |
| EP | 714640 | 6/1996 |
| EP | 756853 | 2/1997 |
| EP | 1032329 | 9/2000 |
| WO | WO 00/12175 | 3/2000 |
| WO | WO 01/41678 | 6/2001 |
| WO | WO2005046526 | 5/2005 |

OTHER PUBLICATIONS

Regar et al., 2001. Stent development and local drug delivery. British Medical Bulletin, vol. 59:277-248.

Refractory Metals Forum: Rhenium and Its Alloys, B.D. Bryskin.

The Effect of Annealing Practice on the Structure and Mechanical Properties of P/M MO—47.5% Re Alloy. John A. Shields, Jr. Climax Specialty Metals, Cleveland, OH 44117.

Delute Mo-Re Alloys—A Critical Evaluation of Their Comparative Mechanical Properties, J. Watsworth, T.T. Nieg, and J.J. Stephens.

Technology Status of Molybdenum and Tungsten Alloys, W.D. Klopp. Materials Consultant, 1542 Mendelssohn Dr., Westlake, OH 44145.

The Alloys of Rhenium with Molybdenum or with Tungsten and Having Good High Temperature Properties, G.A. Geach and J.E. Hughes.

Behaviour of Tungsten, Molybdenum, and Alloys under Unusual Heating Conditions, Ralf Eck, Hubert Bildstein, Fritz Simader, Roland Stickler, Josef Tinzl.

Rhenium and Molybdenum/Tungsten Based Alloys: An Overview of Database, Boris D. Bryskin and Jan C. Carlen.

Mechanical Properties of Mo-Re Alloys at Different Test Temperatures, A.V. Abramyan, N.N. Morgunova, S.A. Golovanenko, and N.I. Kazakova.

Needles, Sutures and Knots, Part III; Specific Suture Materials Al Sherbeeny,M., MD, vol. 1, Jul. 2004

Microsystems for Drug and Gene Delivery, Michael L. Reed, Senior Member, IEEE & Whye-Kei Lye, Member, IEEE , Procedures of the IEEE vol. 92, No. 1, Jan. 2004.

Silicon Micromachined Hollow Microneedles for Transdermal Liquid Transport, Jan J.G.E. Gardeniers, Regina Luttge, Erwin J.W. Berenschot, Meint J. De Boer, Shuki Y. Yeshurun, Meir Hefetz, Ronnyb van't Oever, and Abert van den Berg, Journal of Microelectromechanical Systems, vol. 12, No. 6, Dec. 2003.

A New Method for the Estimation for the Absorption Time of Bioabsorbable Polymers in the Body, D.C.tunc, M. Gockbora and P.Higham/ Stryker Howmedica Osteonics, Advanced Technology Group, Mahwa, NJ 07430 USA.

Synthesis and comparative biodegradability studies of three poly(alkylene succinate)s. D. Bikiaris, G. Papageorgiou, D. Achilias, Laboratory of Organic Chemical Technology, Dept. of Chemistry, Aristotle University of Thessaloniki, GR-541 24, Thessaloniki, Macedonia, Greece.

Silicon Micromachined Hollow Microneedles for Transdermal Liquid Transport, Jan J.G.E. Gardeniers, Regina Luttge, Erwin J.W. Berenschot, Meint J. De Boer, Shuki Y. Yeshurun, Meir Hefetz, Ronnyb van't Oever, and Abert van den Berg, Journal of Microelectromechanical Systems, vol. 12, No. 6, Dec. 2003.

Metals handbook Desk Edition, $2^{nd}$ Edition. Copyright 1998 by ASM Intl.

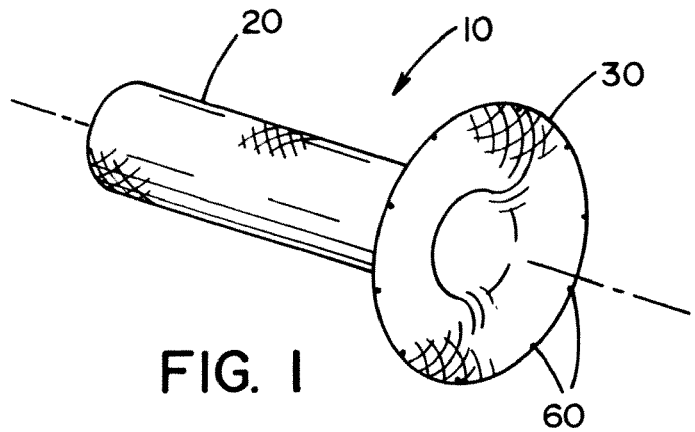
FIG. 1
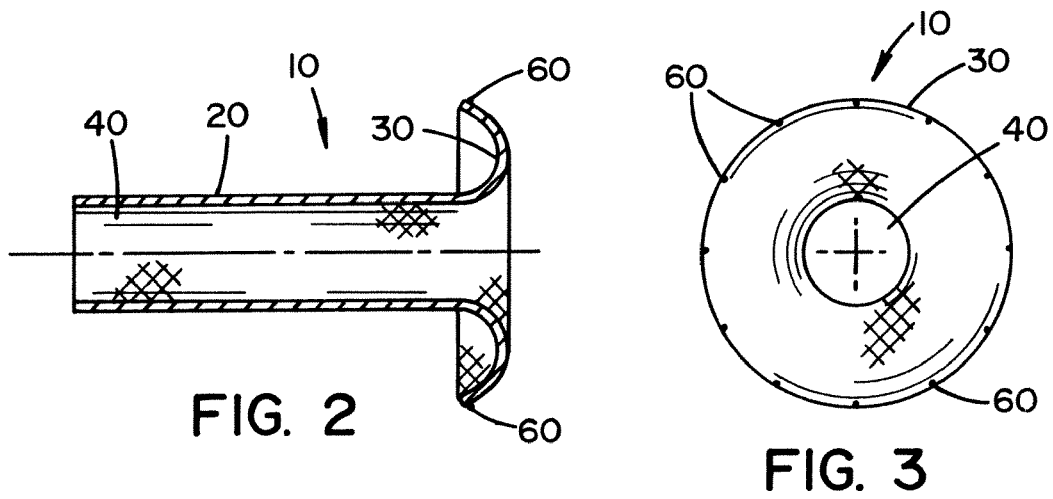
FIG. 2
FIG. 3
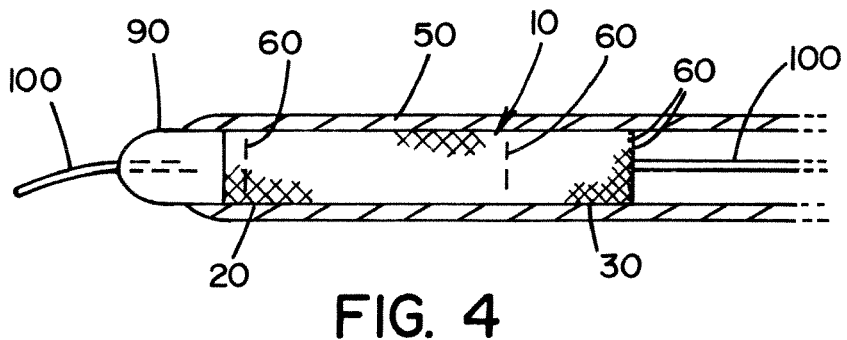
FIG. 4

OSTIAL STENT

The present invention is a continuation of U.S. patent application Ser. No. 11/271,528 filed Nov. 12, 2005 now U.S. Pat. No. 7,455,688 which in turn claims priority on U.S. Provisional Application Ser. Nos. 60/627,421 filed Nov. 12, 2004 entitled "Improved Ostial Stent" and 60/658,289 filed Mar. 3, 2005 entitled "Improved Ostial Stent", both of which are incorporated herein by reference.

The invention relates generally to medical devices, and particularly to a medical device for use within a body, and more particularly to a medical device which is useful in repairing various types of body passageways, even more particularly to a medical device which is useful in repairing blood vessels narrowed or occluded by disease, and still even more particularly to a medical device in the form of an expandable graft for the treatment of stenosis at the ostium of tubular organs.

BACKGROUND OF THE INVENTION

Medical treatment of various illnesses or diseases commonly includes the use of one or more medical devices. Two types of medical devices that are commonly used to repair various types of body passageways are an expandable graft or stent, or a surgical graft. These devices have been implanted in various areas of the mammalian anatomy.

Old age, dietary habits and primary genetics can also lead to a common disease, atherosclerosis. Atherosclerotic plaques and blockages consist of lipids, fibroblasts and fibrin that proliferate and cause obstruction of a vessel. As the obstruction grows, the blood flow diminishes and reaches a level that is insufficient to meet the biological needs of one or more organs. The end result is defined as ischemia.

One purpose of a stent is to open a blocked or partially blocked body passageway. When a stent is used in a blood vessel, the stent is used to open the occluded vessel to achieve improved blood flow which is necessary to provide for the anatomical function of an organ. The procedure of opening a blocked or partially blocked body passageway commonly includes the use of one or more stents in combination with other medical devices such as, but not limited to, an introducer sheath, a guiding catheter, a guide wire, an angioplasty balloon, etc.

The use of stents in blood vessels and other structures in the body has become a well established clinical procedure over the past several years. The equipment and techniques for deploying stents inside blood vessels are well established. There are very few dedicated devices or techniques available for stenting the ostium of blood vessels. Most stents currently available are very difficult to position in the ostium of arteries; since the stent is either inserted too far leaving a critical portion of a lesion uncovered, or the stent protrudes too far out into a major blood vessel such as the aorta or the left main coronary artery. This problem occurs with balloon expandable, as well as self-expanding stents.

Several stents are known to the art. MacGregor, U.S. Pat. No. 4,994,071, discloses a stent having an enlarged end (bifurcation). Maginot, U.S. Pat. No. 5,456,712, discloses a flanged stent member. Mori, U.S. Pat. No. 5,466,242, discloses a shape memory alloy stent where a portion of the stent linearly flares in a funnel/conical shape to hold the stent in place. Lam, U.S. Pat. No. 5,607,444 discloses a specialized ostial stent for repairing vessels at bifurcations. Yadav, U.S. Pat. No. 6,293,964 discloses a specialized ostial stent having a plurality of flat flaring members that are used to hold the stent in the ostia. All of the above-identified stent designs and methodology of use are incorporated herein by reference.

SUMMARY OF THE INVENTION

The invention relates generally to medical devices, and particularly to a medical device for use within a body, and more particularly to a medical device which is useful in repairing various types of body passageways. In one non-limiting embodiment of the invention, the invention relates to a medical device in the form of an expandable graft which is useful in repairing blood vessels or other types of body passageways that have been narrowed or occluded by disease. In another and/or alternative non-limiting embodiment of the invention, the invention relates to a medical device in the form of an expandable graft for the treatment of stenosis at the ostium of tubular organs. In still another and/or alternative non-limiting embodiment of the invention, the invention relates to a medical device in the form of an expandable graft designed for introduction into a tubular organ in a body; however, it can be appreciated that the medical device can be used in other regions of a body. The medical device can be used in the treatment of stenosis at the ostium of tubular organs and more particularly of blood vessels. The medical device includes an expandable body portion, and a flaring end section that is capable of self flaring and/or being flared. As defined herein, the term "body passageway" is defined to be any passageway or cavity in a living organism (e.g., bile duct, bronchiole tubes, nasal cavity, blood vessels, heart, esophagus, trachea, stomach, fallopian tube, uterus, ureter, urethra, the intestines, lymphatic vessels, nasal passageways, eustachian tube, acoustic meatus, etc.). The techniques employed to deliver the medical device to a treatment area include, but are not limited to, angioplasty, vascular anastomoses, transplantation, implantation, subcutaneous introduction, minimally invasive surgical procedures, and any combinations thereof. As can be appreciated, other or additional techniques may be used. For vascular applications, the term "body passageway" primarily refers to blood vessels and chambers in the heart. In one non-limiting application of the medical device of the present invention, the medical device can be designed to treat a stenosis at the ostium of a body passageway. In such an application, the medical device in the form of an expandable graft is placed within the body passageway with its flaring section at the ostium, the flaring section is caused to flare and/or self-flares, and the remainder of the body of the expandable graft is expanded or self expands. The flaring of the flaring section can be achieved at least partially at the same time and/or at least partially at a different time from the expansion of the body portion.

In one non-limiting aspect of the invention, the expandable body portion of the medical device is capable of radial expansion, by self-expansion and/or balloon expansion; however, other types of expansion can be used. The expandable body portion of the medical device can include geometric patterns or structural configurations that facilitate in the radial expansion of the expandable body portion. The expandable body portion of the medical device typically has sufficient radial strength to retain its expanded cross-sectional area after expansion. In one non-limiting design, the medical device includes a material having a low metal-to-opening ratio. In one non-limiting embodiment of the invention, the medical device can be balloon expandable and/or self-expanding; or expanded in another manner. In one non-limiting example, a balloon-expandable medical device can be loaded onto a balloon of a balloon dilatation catheter with the flaring section unexpanded and substantially parallel to the longitudinal axis of the body of the medical device. The medical device can be placed upon the balloon with the flaring section on or adjacent to the proximal portion of the balloon and the body loaded on the middle or distal portion of the balloon; however, this is not required. There may be applications where this position of the medical device on the balloon is reversed. As can be appreciated, one or more balloons can be used to at least partially expand the medical device. In one non-limiting specific arrangement, a single balloon is used to expand one or more regions of the medical device. In another and/or alternative non-limiting specific arrangement, at least two balloons are used to at least partially expand the medical device. Typically the two balloons expand to different shapes and/or sizes. For instance, one balloon can be designed to at least partially expand at least a portion of the body portion, and another balloon can be designed to at least partially expand at least a portion of the flaring section of the medical device. When one balloon is used, the balloon can be repositioned in the medical device to expand different regions of the medical device; however, this is not required. In still another and/or alternative non-limiting specific arrangement, a balloon that includes two or more sections can be used to at least partially expand the medical device. For instance, the balloon can be designed to be divided into at least two sections that expand to different sizes and/or shapes. The medical device is positioned on the balloon such that different sections of the balloon, when expanded, affect the expansion of the medical device in different ways. For example, one section of the balloon can be designed to at least partially expand at least a portion of the body portion, and another section of the balloon can be designed to at least partially expand at least a portion of the flaring section of the medical device. As can be appreciated, many other balloon configurations and/or medical device positioning of the balloon can be used to at least partially expand the medical device. As can also be appreciated, the one or more balloons can be used to at least partially expand the medical device at different times (e.g., initially at least partially expand the body portion and then at least partially expand the flaring section, etc.). The balloon and medical device can be advanced to a desired site by use of a guiding catheter and a guide wire; however, other positioning mechanisms can be used. After the medical device is positioned at a desired site in the tubular organ, it can be deployed in a manner to permit the flaring section to flare or expand at the ostium. The flaring of the flaring section can occur before, during and/or after the expansion of the non-flaring portion of the medical device in the tubular organ. When the medical device is at least partially formed of a spring-like, shape memory, or similar material so as to be at least partially self-expanding, the medical device can be secured to a delivery catheter in an unexpanded state or positioned in a delivery sheath and/or maintained in such shape by another or additional physical hindrance and then advanced through a guiding catheter or protective sheath to a desired location. As can be appreciated, other mechanisms can be used to advance the medical device to a desired site in a tubular organ. There are a number of known delivery systems for delivery of a self-expanding medical device. Non-limiting examples of such delivery systems than can be used to delivery the medical device of the present invention to a desired site in a tubular organ are disclosed in U.S. Pat. Nos. 4,886,062, 4,913,141, 5,019,085, 5,147,370, 5,372,600, 5,507,768, 5,549,635, 5,607,467, 5,632,760, 5,643,278, and 5,669,932, all of which are incorporated herein by reference. Once the medical device is positioned in a desired location, the medical device is typically released from the delivery catheter, sheath or the like.

In another and/or alternative non-limiting aspect of the invention, the medical device can be designed to be in the form of a stent that is configured to have at least two sections, an expandable body portion that has a generally constant diameter in an expanded state, and a flaring section with multiple different diameters when in an expanded state; however, it can be appreciated that the body portion can have a variable diameter over the length of the body portion. The medical device can be made of a uniform material, or one or more regions of the medical device can be formed of different materials (e.g., metal, polymer, plastic, fiber reinforced material, etc.). Typically the body portion and the flaring portion are formed of the same or similar materials so as to 1) simplify the manufacturing process associated with the medical device and/or 2) inhibit or prevent corrosion at the joint between two of more different materials. One or more portions of the medical device can be formed of a biostable material and/or a non-biostable material (e.g., biodegradable, bioabsorbable, etc.). Some non-limiting metals that can be used to at least partially form the medical device include, but are not limited to, aluminum, barium, bismuth, calcium, cobalt, copper, chromium, gold, iron, stainless steel, titanium, vanadium, nickel, zirconium, niobium, lead, molybdenum, platinum, magnesium, yttrium, calcium, rare earth metals, rhenium, zinc, silver, depleted radioactive elements, tantalum, tungsten and/or alloys thereof (e.g., nitinol, etc.). In one non-limiting example, one or more portions of the expandable body portion and/or flaring sections can be fabricated from material that 1) has no or substantially no shape memory characteristics (e.g., stainless steel, cobalt, chromium, magnesium, rhenium, zinc, titanium, tantalum, zirconium, etc.), and/or 2) has shape-memory characteristics (e.g., nickel-titanium alloy (nitinol), or another metallic or non-metallic material which possesses the characteristic of shape memory). The sections of the medical device can have a uniform architectural configuration, or can have differing architectural configurations. Each of the sections of the medical device can be formed of a single part or formed of multiple parts which have been attached together. When a section of the medical device is formed of multiple parts, typically the section is formed into one continuous piece; however, this is not required. In another and/or alternative non-limiting example, one or more portions of the medical device can include a bistable construction. In such a design, the medical device has two or more stable configurations, including a first stable configuration with a first cross-sectional shape and a second stable configuration with a second cross-sectional shape. All or a portion of the medical device can include the bistable construction. The bistable construction can result in a generally uniform change in shape of the medical device, or one portion of the medical device can change into one or more configurations and one or more other portions of the medical device can change into one or more other configurations.

In still another and/or alternative non-limiting aspect of the invention, the expandable body portion of the medical device generally constitutes a larger portion of the longitudinal length of the medical device; however, this is not required. The flaring section of the medical device in an expanded state has multiple different diameters resulting in an outward flare of the flaring section with respect to the longitudinal axis of the medical device. This outward flare results in the end of the flaring section typically having the largest diameter of the medical device when the flaring section has been expanded. In one non-limiting embodiment, the flaring section constitutes less than a majority of the longitudinal length of the medical device and the expandable body portion constitutes a majority of the longitudinal length of the medical device. In one non-limiting aspect of this embodiment, the flaring section constitutes up to about 40 percent of the longitudinal length of the medical device and the expandable body portion constitutes at least about 60 percent of the longitudinal length of the medical device. In another and/or alternative non-limiting aspect of this embodiment, the flaring section constitutes up to about 25 percent of the longitudinal length of the medical device and the expandable body portion constitutes at least about 75 percent of the longitudinal length of the medical device. In still another and/or alternative non-limiting aspect of this embodiment, the flaring section constitutes up to about 20 percent of the longitudinal length of the medical device and the expandable body portion constitutes at least about 80 percent of the longitudinal length of the medical device. In yet another and/or alternative non-limiting aspect of this embodiment, the flaring section constitutes up to about 15 percent of the longitudinal length of the medical device and the expandable body portion constitutes at least about 85 percent of the longitudinal length of the medical device. As can be appreciated, other length ratios of the flaring section and expandable body portion can be used. In one non-limiting design of the medical device for use in a blood vessel, the expandable body portion is about 5-20 mm and the flaring section is about 0.5-4 mm. In another and/or alternative non-limiting design of the medical device for use in a blood vessel, the expandable body portion is about 7-18 mm and the flaring section is about 1-3 mm. In still another and/or alternative non-limiting design of the medical device for use in a blood vessel, the expandable body portion is about 8-16 mm and the flaring section is about 1-2 mm. As can be appreciated, other length of the flaring section and expandable body portion of the medical device can be used. In still another and/or alternative non-limiting embodiment of the invention, the flaring portion of the medical device is designed to have a maximum expanded diameter of about 5-14 mm, typically about 7-12 mm, and more typically about 9-11 mm. This maximum diameter of the flaring section enables the medical device to be positioned in a variety of vascular passageways and to provide substantially complete coverage of the region about the ostium. In yet another and/or alternative non-limiting embodiment of the invention, the maximum diameter of the expanded flaring section of the medical device is at least about 25% greater than the maximum diameter of the expanded body portion. In still another and/or alternative non-limiting embodiment, the flaring section, in an expanded state, is large enough in size to cover the area about the ostium. In some prior art designs, the flaring section of the stent was not large enough to cover at least a portion of the body passageway surrounding the ostium. One such stent is disclosed in US 2003/0083734 published May 1, 2003, which is incorporated herein by reference. As shown in FIG. 3, the edge of the flaring section of the stent is positioned flushed with the blood vessel about the ostium. As such, the flaring section does not overlay any portion of the blood vessel about the ostium. The medical device of the present invention is designed to have a flaring section sized so that at least 0.25 mm of the blood vessel about the complete ostium is covered by the flaring section when the flaring section is expanded. This novel configuration better secures the medical device in the body passageway and/or can reduce the incidence of restenosis. In one non-limiting design, the medical device of the present invention is designed to have a flaring section sized so that about 0.25-5 mm of the blood vessel about the complete ostium is covered by the flaring section when the flaring section is expanded. In still another non-limiting design, the medical device of the present invention is designed to have a flaring section sized so that about 0.5-4 mm of the blood vessel about the complete ostium is covered by the flaring section when the flaring section is expanded. As can be appreciated, the medical device of the present invention can be designed to have a flaring section sized so that other amounts of the blood vessel about the complete ostium can be covered by the flaring section when the flaring section is expanded. In still another and/or alternative non-limiting embodiment, the flaring section, in an expanded state, has a generally nonlinear rate of flaring over the complete longitudinal length of the flaring section; however, it can be appreciated that the rate of flaring can be linear. In one non-limiting aspect of this embodiment, the rate of nonlinear flaring of the flaring section in the expanded state relative to the longitudinal axis of the medical device is a generally second order rate of curvature. In another and/or alternative non-limiting aspect of this embodiment, the rate of nonlinear flaring of the flaring section in the expanded state relative to the longitudinal axis of the medical device is a generally an exponential rate of curvature. In another and/or alternative non-limiting aspect of this embodiment, the rate of nonlinear flaring of the flaring section in the expanded state relative to the longitudinal axis of the medical device is a plurality of linear flaring rates over the longitudinal length of the flaring section. As can be appreciated, other rates of nonlinear flaring can be used. In still another and/or alternative non-limiting aspect of this embodiment, the maximum angle of flaring of the flaring section, in an expanded state, relative to the longitudinal axis of the medical device is up to about 160°. In yet another and/or alternative non-limiting aspect of this embodiment, the maximum angle of flaring of the flaring section, in an expanded state, relative to the longitudinal axis of the medical device is up to about 130°. In still yet another and/or alternative non-limiting aspect of this embodiment, the maximum angle of flaring of the flaring section, in an expanded state, relative to the longitudinal axis of the medical device is up to about 120°. As can be appreciated, other maximum angles of flaring of the flaring section can be used. The flaring section, in the expanded state, can have one portion that has a greater maximum angle of flaring than another portion. Such non-uniform expansion of the flaring section can result in part from geometry of the body passageway in which the medical device expands. Typically the body passageways on the body do not branch off another body passageway at a 90° angle. Indeed, it is common for a branched tubular organ or vessel to intersect another tubular organ or vessel at an angle other than 90°. As such, the proper coverage of the ostium can be difficult, if not impossible, when using a standard expandable stent. Stent designs that had a flare angle of 90° or less could not fully cover the region about the ostium after the flaring section has been fully expanded. As such, this uncovered region about the ostium can result in vasculature ingrowth, which ingrowth may result in an increased incidence of restenosis. In addition, the inability of the complete edge of the flaring section to cover and contact the region about the ostium is believed to increase the incidence of 1) clotting and/or deposits forming between the flaring section and the surface about the ostium, and/or 2) interference with other medical devices being inserted in and/or moved past the region about ostium. The novel design of the flaring section of the medical device of the present invention overcomes all of the past limitations that were associated with prior ostial designs. The ability of the flaring section to expand at an angle greater than 90° relative to the longitudinal axis of the medical device is a significant improvement over prior stents that had a maximum flare angle of 90° or less (See US 2003/0083734; US 2004/0093058; US 2005/0049678; WO 2005/046526). As such, when a treated body passageway branches off another body passageway at an angle other than 90°, the maximum flare angle of the flaring section of the medical device of the present invention in the expanded state will be less than 90° about one portion about the ostium and greater than 90° about another portion of the ostium. As a result, the flaring section of the medical device of the present invention provides significantly better coverage of the ostium, thus is believed to better facilitate in the inhibition or prevention of restenosis. The flaring section of the medical device of the present invention also enables the flaring section to better and more closely conform to the ostium of the tubular organ, thereby facilitating in firmly securing the medical device at such site. Radial expansion of the body enables the medical device to substantially conform to, and press against, the inner wall and stenosis of a tubular organ or vessel, thereby seating the medical device. The expansion of the flaring section enables the flaring section to fully cover the ostium of the tubular organ. In a further and/or alternative embodiment of the invention, the flaring section and the body portion of the medical device do not have any discontinuities between the body portion and flaring section. Some prior ostial stents included an expanded structural configuration of the body portion that was secured to one or more ends of the stent by a one or more connectors. For instance, the stent design disclosed in Mori, U.S. Pat. No. 5,466,242 includes a transition portion between the body of the stent and one end of the stent, thus forming a non-uniform structural transition between the body and end section of the stent. This type of non-uniform transition can compromise the strength and/or effectiveness of the stent. In other stent designs, one or more ends of the stent did not maintain a uniform structure. Two such stents are disclosed in US 2004/0254627 and US 2005/0154447. These two stents include an end portion that has a plurality of flat flaring members. These flaring members separate from one another; thereby creating a non-uniform end portion in the expanded state. This non-uniform end portion when expanded in a vascular passageway can allow for tissue growth between the flat flaring members, which tissue growth is believed to potentially increase the incidence of restenosis. The medical device of the present invention is designed to overcome both of these past limitations regarding prior stents. The body portion and flaring section of the medical device have a uniform structure. In one non-limiting configuration, the flaring section, in an expanded state, maintains a substantially single and uniform structure. Due to this configuration, tissue growth under the expanded flaring section is substantially inhibited, thereby is believed to facilitate in the inhibition or prevention of restenosis. Typically, at least about 90% of the flaring section, in an expanded state, maintains a substantially single and uniform structure, and more typically at least about 95% of the flaring section, in an expanded state, maintains a substantially single and uniform structure, and even more typically at least about 98% of the flaring section, in an expanded state, maintains a substantially single and uniform structure.

In yet another and/or alternative non-limiting aspect of the invention, the medical device can be fully or partially formed of a base material that has biostable or bioabsorbable properties. The medical device can be at least partially formed of one or more polymers, biological agents, metals (e.g., aluminum, barium, bismuth, calcium, cobalt, copper, chromium, depleted radioactive elements, gold, iron, lead, molybdenum, magnesium, nickel, niobium, platinum, rare earth metals, rhenium, silver, tantalum, titanium, tungsten, vanadium, yttrium, zinc, zirconium, and/or alloys thereof (e.g., stainless steel, nitinol, Cr—Co, Mo—Re, Ta—W, Mg—Zr, Mg—Zn, etc.)), ceramics, and/or fiber reinforced materials (e.g., carbon fiber material, fiberglass, etc.). As can be appreciated; other or additional materials can be used. The medical device generally includes one or more materials that impart the desired properties to the medical device so as to withstand the manufacturing process that is needed to produce the medical device. These manufacturing processes can include, but are not limited to, laser cutting, etching, grinding, water cutting, spark erosion, crimping, annealing, drawing, pilgering, electroplating, electro-polishing, chemical polishing, ion beam deposition or implantation, sputter coating, vacuum deposition, etc.

In still yet another and/or alternative non-limiting aspect of the present invention, the medical device can include and/or be used with a physical hindrance. The physical hindrance can include, but is not limited to, an adhesive, a sheath, a magnet, tape, wire, string, etc. The physical hindrance can be used to 1) physically retain one or more regions of the medical device in a particular form or profile, 2) physically retain the medical device on a particular deployment device, 3) protect one or more surface structures and/or micro-structures on the medical device, and/or 4) form a barrier between one or more surface regions, surface structures and/or micro-structures on the medical device and the fluids in a body passageway. As can be appreciated, the physical hindrance can have other and/or additional functions. The physical hindrance can be a biodegradable material; however, a biostable can also or alternatively be used. The physical hindrance can be designed to withstand sterilization of the medical device; however, this is not required. The physical hindrance can be applied to, included in and/or be used in conjunction with one or more medical devices; however, this is not required. Additionally or alternatively, the physical hindrance can be designed to be used with and/or conjunction with a medical device for a limited period of time and then 1) disengage from the medical device after the medical device has been partially or fully deployed and/or 2) dissolve and/or degrade during and/or after the medical device has been partially or fully deployed; however, this is not required. Additionally or alternatively, the physical hindrance can be designed and/or be formulated to be temporarily used with a medical device to facilitate in the deployment of the medical device; however, this is not required. In one non-limiting use of the physical hindrance, the physical hindrance is designed and/or formulated to at least partially secure the medical device to another device that is used to at least partially transport the medical device to a location for treatment. In another and/or alternative non-limiting use of the physical hindrance, the physical hindrance is designed and/or formulated to at least partially maintain the medical device in a particular shape or form until the medical device is at least partially positioned in a treatment location. In still another and/or alternative non-limiting use of the physical hindrance, the physical hindrance is designed and/or formulated to at least partially maintain and/or secure the medical device to a medical instrument or other type of device until the medical device is at least partially positioned in a treatment location. The physical hindrance can also or alternatively be designed and/or formulated to be used with the medical device to facilitate in the use of the medical device. In one non-limiting use of the physical hindrance, the physical hindrance is designed and/or formulated to at least partially secure a medical device to a treatment area so as to facilitate in maintaining the medical device at the treatment area. For instance, the physical hindrance can be used in such use to facilitate in maintaining a medical device on or at a treatment area until the medical device is properly secured to the treatment area by sutures, stitches, screws, nails, rod, etc. Additionally or alternatively, the physical hindrance can be used to facilitate in maintaining a medical device on or at a treatment area until the medical device has a) partially or fully been expanded and/orb) partially or fully accomplished its objective. The physical hindrance can be a biocompatible material so as to not cause unanticipated adverse effects when properly used. The physical hindrance can be biostable or biodegradable (e.g., degrades and/or is absorbed, etc.). When the physical hindrance includes or is primarily formed of one or more adhesives, the one or more adhesive can be applied to the medical device by, but not limited to, spraying (e.g., atomizing spray techniques, etc.), dip coating, roll coating, sonication, brushing, plasma deposition, and/or depositing by vapor deposition, brushing, painting, etc.) on the medical device. The physical hindrance can also or alternatively form at least a part of the medical device. One or more regions and/or surfaces of a medical device can also or alternatively include the physical hindrance. The physical hindrance can include one or more biological agents and/or other materials (e.g., marker material, polymer, etc.); however, this is not required. When the physical hindrance is or includes an adhesive, the adhesive can be formulated to controllably release one or more biological agents a) included in the adhesive, b) coated on the medical device and/or adhesive, and/or c) contained within the medical device; however, this is not required. The adhesive can also or alternatively control the release of one or more biological agents located on and/or contained in the medical device by forming a penetrable or non-penetrable barrier to such biological agents; however, this is not required. The adhesive can include and/or be mixed with one or more polymers; however, this is not required. The one or more polymers, when used, can be used to 1) control the time of adhesion provided by said adhesive, 2) control the rate of degradation of the adhesive, and/or 3) control the rate of release of one or more biological agents released from the adhesive and/or diffusing or penetrating through the adhesive layer; however, this is not required. When the physical hindrance includes a sheath, the sheath can be designed to partially or fully encircle the medical device. The sheath can be designed to be physically removed from the medical device after the medical device is deployed to a treatment area; however, this is not required. The sheath can be at least partially formed of a biostable material. The sheath can be at least partially formed of a biodegradable material that at least partially degrades over time to at least partially expose one or more surface regions, micro-structures and/or surface structures of the medical device; however, this is not required. The sheath can include and/or be at least partially coated with one or more biological agents; however, this is not required. The sheath can include one or more polymers; however, this is not required. The one or more polymers, when used, can be used for a variety of reasons such as, but not limited to, 1) forming a portion of the sheath, 2) improving a physical property of the sheath (e.g., improve strength, improve durability, improve biocapatability, reduce friction, etc.), and/or 3) at least partially controlling a release rate of one or more biological agents from the sheath. As can be appreciated, the one or more polymers, when used, can have other or additional uses. In one non-limiting example, the medical device that is in the form of an expandable graft can be deployed in its final destination by an expansion device (e.g., balloon, etc.) and/or by use of a shape memory material. As can be appreciated, medical devices that include heat sensitive and/or shape memory materials can be at least partially expanded by a balloon and/or another type of expansion device. The removal, degradation and/or elimination of the physical hindrance from the medical device enables the medical device to at least partially assume its expanded state. When the physical hindrance includes an adhesive and the medical device is at least partially expanded by a balloon and/or another type of expansion device, the balloon and/or another type of expansion device can be expanded to at least partially cause the adhesive to break, weaken, etc.; thereby enabling the medical device to at least partially expand; however, this is not required.

In a further and/or alternative non-limiting aspect of the present invention, one or more biological agents are used with the medical device to facilitate in the success of the medical device and/or treated area. The term "biological agent" includes, but is not limited to, a substance, drug or otherwise formulated and/or designed to prevent, inhibit and/or treat one or more biological problems, and/or to promote the healing in a treated area. Non-limiting examples of biological problems that can be addressed by one or more biological agents include, but are not limited to, viral, fungus and/or bacteria infection; vascular diseases and/or disorders; digestive diseases and/or disorders; reproductive diseases and/or disorders; lymphatic diseases and/or disorders; cancer; implant rejection; pain; nausea; swelling; arthritis; bone diseases and/or disorders; organ failure; immunity diseases and/or disorders; cholesterol problems; blood diseases and/or disorders; lung diseases and/or disorders; heart diseases and/or disorders; brain diseases and/or disorders; neuralgia diseases and/or disorders; kidney diseases and/or disorders; ulcers; liver diseases and/or disorders; intestinal diseases and/or disorders; gallbladder diseases and/or disorders; pancreatic diseases and/or disorders; psychological disorders; respiratory diseases and/or disorders; gland diseases and/or disorders; skin diseases and/or disorders; hearing diseases and/or disorders; oral diseases and/or disorders; nasal diseases and/or disorders; eye diseases and/or disorders; fatigue; genetic diseases and/or disorders; burns; scaring and/or scars; trauma; weight diseases and/or disorders; addiction diseases and/or disorders; hair loss; cramps; muscle spasms; tissue repair; and/or the like. Non-limiting examples of biological agents that can be used include, but are not limited to, 5-Fluorouracil and/or derivatives thereof; 5-Phenylmethimazole and/or derivatives thereof; ACE inhibitors and/or derivatives thereof; acenocoumarol and/or derivatives thereof; acyclovir and/or derivatives thereof; actilyse and/or derivatives thereof; adrenocorticotropic hormone and/or derivatives thereof; adriamycin and/or derivatives thereof; agents that modulate intracellular $Ca_{2+}$ transport such as L-type (e.g., diltiazem, nifedipine, verapamil, etc.) or T-type $Ca_{2+}$ channel blockers (e.g., amiloride, etc.); alpha-adrenergic blocking agents and/or derivatives thereof; alteplase and/or derivatives thereof; amino glycosides and/or derivatives thereof (e.g., gentamycin, tobramycin, etc.); angiopeptin and/or derivatives thereof; angiostatic steroid and/or derivatives thereof; angiotensin II receptor antagonists and/or derivatives thereof; anistreplase and/or derivatives thereof; antagonists of vascular epithelial growth factor and/or derivatives thereof; anti-biotics; anti-coagulant compounds and/or derivatives thereof; anti-fibrosis compounds and/or derivatives thereof; anti-fungal compounds and/or derivatives thereof; anti-inflammatory compounds and/or derivatives thereof; Anti-Invasive Factor and/or derivatives thereof, anti-metabolite compounds and/or derivatives thereof (e.g., staurosporin, trichothecenes, and modified diphtheria and ricin toxins, Pseudomonas exotoxin, etc.); anti-matrix compounds and/or derivatives thereof (e.g., colchicine, tamoxifen, etc.); anti-microbial agents and/or derivatives thereof; anti-migratory agents and/or derivatives thereof (e.g., caffeic acid derivatives, nilvadipine, etc.); anti-mitotic compounds and/or derivatives thereof; anti-neoplastic compounds and/or derivatives thereof; anti-oxidants and/or derivatives thereof; anti-platelet compounds and/or derivatives thereof; anti-proliferative and/or derivatives thereof; anti-thrombogenic agents and/or derivatives thereof; argatroban and/or derivatives thereof; ap-1 inhibitors and/or derivatives thereof (e.g., for tyrosine kinase, protein kinase C, myosin light chain kinase, $Ca_{2+}$/calmodulin kinase II, casein kinase II, etc.); aspirin and/or derivatives thereof; azathioprine and/or derivatives thereof; β-Estradiol and/or derivatives thereof; β-1-anticollagenase and/or derivatives thereof; calcium channel blockers and/or derivatives thereof; calmodulin antagonists and/or derivatives thereof (e.g., $H_7$, etc.); CAPTOPRIL and/or derivatives thereof; cartilage-derived inhibitor and/or derivatives thereof; ChIMP-3 and/or derivatives thereof; cephalosporin and/or derivatives thereof (e.g., cefadroxil, cefazolin, cefaclor, etc.); chloroquine and/or derivatives thereof; chemotherapeutic compounds and/or derivatives thereof (e.g., 5-fluorouracil, vincristine, vinblastine, cisplatin, doxyrubicin, adriamycin, tamocifen, etc.); chymostatin and/or derivatives thereof; CILAZAPRIL and/or derivatives thereof; clopidigrel and/or derivatives thereof; clotrimazole and/or derivatives thereof; colchicine and/or derivatives thereof; cortisone and/or derivatives thereof; coumadin and/or derivatives thereof; curacin-A and/or derivatives thereof; cyclosporine and/or derivatives thereof; cytochalasin and/or derivatives thereof (e.g., cytochalasin A, cytochalasin B, cytochalasin C, cytochalasin D, cytochalasin E, cytochalasin F, cytochalasin G, cytochalasin H, cytochalasin J, cytochalasin K, cytochalasin L, cytochalasin M, cytochalasin N, cytochalasin O, cytochalasin P, cytochalasin Q, cytochalasin R, cytochalasin S, chaetoglobosin A, chaetoglobosin B, chaetoglobosin C, chaetoglobosin D, chaetoglobosin E, chaetoglobosin F, chaetoglobosin G, chaetoglobosin J, chaetoglobosin K, deoxaphomin, proxiphomin, protophomin, zygosporin D, zygosporin E, zygosporin F, zygosporin G, aspochalasin B, aspochalasin C, aspochalasin D, etc.); cytokines and/or derivatives thereof; desirudin and/or derivatives thereof; dexamethazone and/or derivatives thereof; dipyridamole and/or derivatives thereof; eminase and or derivatives thereof; endothelin and/or derivatives thereof; endothelial growth factor and/or derivatives thereof; epidermal growth factor and/or derivatives thereof; epothilone and/or derivatives thereof; estramustine and/or derivatives thereof; estrogen and/or derivatives thereof; fenoprofen and/or derivatives thereof; fluorouracil and/or derivatives thereof; flucytosine and/or derivatives thereof; forskolin and/or derivatives thereof; ganciclovir and/or derivatives thereof; glucocorticoids and/or derivatives thereof (e.g., dexamethasone, betamethasone, etc.); glycoprotein IIb/IIIa platelet membrane receptor antibody and/, or derivatives thereof; GM-CSF and/or derivatives thereof; griseofulvin and/or derivatives thereof; growth factors and/or derivatives thereof (e.g., VEGF; TGF; IGF; PDGF; FGF, etc.); growth hormone and/or derivatives thereof; heparin and/or derivatives thereof; hirudin and/or derivatives thereof; hyaluronate and/or derivatives thereof; hydrocortisone and/or derivatives thereof; ibuprofen and/or derivatives thereof; immunosuppressive agents and/or derivatives thereof (e.g., adrenocorticosteroids, cyclosporine, etc.); indomethacin and/or derivatives thereof; inhibitors of the sodium/calcium antiporter and/or derivatives thereof (e.g., amiloride, etc.); inhibitors of the $IP_3$ receptor and/or derivatives thereof; inhibitors of the sodium/hydrogen antiporter and/or derivatives thereof (e.g., amiloride and derivatives thereof, etc.); insulin and/or derivatives thereof; Interferon alpha 2 Macroglobulin and/or derivatives thereof; ketoconazole and/or derivatives thereof; Lepirudin and/or derivatives thereof; LISINOPRIL and or derivatives thereof; LOVASTATIN and/or derivatives thereof; marevan and/or derivatives thereof; mefloquine and/or derivatives thereof; metalloproteinase inhibitors and/or derivatives thereof; methotrexate and/or derivatives thereof; metronidazole and/or derivatives thereof; miconazole and/or derivatives thereof; monoclonal antibodies and/or derivatives thereof; mutamycin and/or derivatives thereof; naproxen and/or derivatives thereof; nitric oxide and/or derivatives thereof; nitroprusside and/or derivatives thereof; nucleic acid analogues and/or derivatives thereof (e.g., peptide nucleic acids, etc.); nystatin and/or derivatives thereof; oligonucleotides and/or derivatives thereof; paclitaxel and/or derivatives thereof; penicillin and/or derivatives thereof; pentamidine isethionate and/or derivatives thereof; phenindione and/or derivatives thereof; phenylbutazone and/or derivatives thereof; phosphodiesterase inhibitors and/or derivatives thereof; Plasminogen Activator Inhibitor-1 and/or derivatives thereof; Plasminogen Activator Inhibitor-2 and/or derivatives thereof; Platelet Factor 4 and/or derivatives thereof; platelet derived growth factor and/or derivatives thereof; plavix and/or derivatives thereof; POSTMI 75 and/or derivatives thereof; prednisone and/or derivatives thereof; prednisolone and/or derivatives thereof; probucol and/or derivatives thereof; progesterone and/or derivatives thereof; prostacyclin and/or derivatives thereof; prostaglandin inhibitors and/or derivatives thereof; protamine and/or derivatives thereof; protease and/or derivatives thereof; protein kinase inhibitors and/or derivatives thereof (e.g., staurosporin, etc.); quinine and/or derivatives thereof; radioactive agents and/or derivatives thereof (e.g., Cu-64, Ca-67, Cs-131, Ga-68, Zr-89, Ku-97, Tc-99m, Rh-105, Pd-103, Pd-109, In-111, I-123, I-125, I-131, Re-186, Re-188, Au-198, Au-199, Pb-203, At-211, Pb-212, Bi-212, $H_3P^{32}O_4$, etc.); rapamycin and/or derivatives thereof; receptor antagonists for histamine and/or derivatives thereof; refludan and/or derivatives thereof; retinoic acids and/or derivatives thereof; revasc and/or derivatives thereof; rifamycin and/or derivatives thereof; sense or anti-sense oligonucleotides and/or derivatives thereof (e.g., DNA, RNA, plasmid DNA, plasmid RNA, etc.); seramin and/or derivatives thereof; steroids; seramin and/or derivatives thereof; serotonin and/or derivatives thereof; serotonin blockers and/or derivatives thereof; streptokinase and/or derivatives thereof; sulfasalazine and/or derivatives thereof; sulfonamides and/or derivatives thereof (e.g., sulfamethoxazole, etc.); sulphated chitin derivatives; Sulphated Polysaccharide Peptidoglycan Complex and/or derivatives thereof; $T_{H1}$ and/or derivatives thereof (e.g., Interleukins-2, -12, and -15, gamma interferon, etc.); thioprotese inhibitors and/or derivatives thereof; taxol and/or derivatives thereof (e.g., taxotere, baccatin, 10-deacetyltaxol, 7-xylosyl-10-deacetyltaxol, cephalomannine, 10-deacetyl-7-epitaxol, 7 epitaxol, 10-deacetylbaccatin III, 10-deacetylcephaolmannine, etc.); ticlid and/or derivatives thereof; ticlopidine and/or derivatives thereof; tick anti-coagulant peptide and/or derivatives thereof; thioprotese inhibitors and/or derivatives thereof; thyroid hormone and/or derivatives thereof; Tissue Inhibitor of Metalloproteinase-1 and/or derivatives thereof; Tissue Inhibitor of Metalloproteinase-2 and/or derivatives thereof; tissue plasma activators; TNF and/or derivatives thereof, tocopherol and/or derivatives thereof; toxins and/or derivatives thereof; tranilast and/or derivatives thereof; transforming growth factors alpha and beta and/or derivatives thereof; trapidil and/or derivatives thereof; triazolopyrimidine and/or derivatives thereof; vapiprost and/or derivatives thereof; vinblastine and/or derivatives thereof; vincristine and/or derivatives thereof; zidovudine and/or derivatives thereof. As can be appreciated, the biological agent can include one or more derivatives of the above listed compounds and/or other compounds. In one non-limiting embodiment, the biological agent includes, but is not limited to, trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. The type and/or amount of biological agent included on, in and/or in conjunction with the medical device is generally selected for the treatment of one or more medical treatments. Typically the amount of biological agent included on, in and/or used in conjunction with the medical device is about 0.01-100 ug per $mm^2$; however, other amounts can be used. The amount of two of more biological agents on, in and/or used in conjunction with the medical device can be the same or different. In one non-limiting example, the medical device can be coated with and/or includes one or more biological agents such as, but not limited to, trapidil and/or trapidil derivatives, taxol, taxol derivatives (e.g., taxotere, baccatin, 10-deacetyltaxol, 7-xylosyl-10-deacetyltaxol, cephalomannine, 10-deacetyl-7-epitaxol, 7 epitaxol, 10-deacetylbaccatin III, 10-deacetylcephaolmannine, etc.), cytochalasin, cytochalasin derivatives (e.g., cytochalasin A, cytochalasin B, cytochalasin C, cytochalasin D, cytochalasin E, cytochalasin F, cytochalasin G, cytochalasin H, cytochalasin J, cytochalasin K, cytochalasin L, cytochalasin M, cytochalasin N, cytochalasin O, cytochalasin P, cytochalasin Q, cytochalasin R, cytochalasin S, chaetoglobosin A, chaetoglobosin B, chaetoglobosin C, chaetoglobosin D, chaetoglobosin E, chaetoglobosin F, chaetoglobosin G, chaetoglobosin J, chaetoglobosin K, deoxaphomin, proxiphomin, protophomin, zygosporin D, zygosporin E, zygosporin F, zygosporin G, aspochalasin B, aspochalasin C, aspochalasin D, etc.), paclitaxel, paclitaxel derivatives, rapamycin, rapamycin derivatives, 5-Phenylmethimazole, 5-Phenylmethimazole derivatives, GM-CSF (granulo-cyte-macrophage colony-stimulating-factor), GM-CSF derivatives, or combinations thereof. In one non-limiting embodiment of the invention, the medical device can be partially of fully coated with one or more biological agents to facilitate in the success of a particular medical procedure. The one or more biological agents can be coated on the medical device by a variety of mechanisms such as, but not limited to, spraying (e.g., atomizing spray techniques, etc.), dip coating, roll coating, sonication, brushing, plasma deposition, depositing by vapor deposition. In another and/or alternative non-limiting embodiment of the invention, the type and/or amount of biological agent included on, in and/or in conjunction with the medical device is generally selected for the treatment of one or more medical treatments. Typically the amount of biological agent included on, in and/or used in conjunction with the medical device is about 0.01-100 ug per $mm^2$; however, other amounts can be used. The amount of two of more biological agents on, in and/or used in conjunction with the medical device can be the same or different. For instance, one or more biological agents can be coated on, and/or incorporated in one or more portions of the medical device to provide local and/or systemic delivery of one or more biological agents in and/or to a body passageway to a) inhibit or prevent thrombosis, in-stent restenosis, vascular narrowing and/or restenosis after the medical device has been inserted in and/or connected to a body passageway, b) at least partially passivate, remove and/or dissolve lipids, fibroblast, fibrin, etc. in a body passageway so as to at least partially remove such materials and/or to passivate such vulnerable materials (e.g., vulnerable plaque, etc.) in the body passageway in the region of the medical device and/or down stream of the medical device. As can be appreciated, the one or more biological agents can have many other or additional uses. In another non-limiting example, the medical device is coated with and/or includes one or more biological agents such as, but not limited to, trapidil and/or trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. In still another non-limiting example, the medical device is coated with and/or includes one or more biological agents such as, but not limited trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof, and one or more additional biological agents, such as, but not limited to, biological agents associated with thrombolytics, vasodilators, anti-hypertensive agents, anti-microbial or anti-biotic, anti-mitotic, anti-proliferative, anti-secretory agents, non-steroidal anti-inflammatory drugs, immunosuppressive agents, growth factors and growth factor antagonists, antitumor and/or chemotherapeutic agents, anti-polymerases, anti-viral agents, antibody targeted therapy agents, hormones, anti-oxidants, biologic components, radio-therapeutic agents, radiopaque agents and/or radio-labeled agents.

In a further and/or alternative non-limiting aspect of the present invention, the one or more biological agents on and/or in the medical device, when used on the medical device, can be released in a controlled manner so the area in question to be treated is provided with the desired dosage of biological agent over a sustained period of time. As can be appreciated, controlled release of one or more biological agents on the medical device is not always required and/or desirable. As such, one or more of the biological agents on and/or in the medical device can be uncontrollably released from the medical device during and/or after insertion of the medical device in the treatment area. It can also be appreciated that one or more biological agents on and/or in the medical device can be controllably released from the medical device and one or more biological agents on and/or in the medical device can be uncontrollably released from the medical device. It can also be appreciated that one or more biological agents on and/or in one region of the medical device can be controllably released from the medical device and one or more biological agents on and/or in the medical device can be uncontrollably released from another region on the medical device. As such, the medical device can be designed such that 1) all the biological agent on and/or in the medical device is controllably released, 2) some of the biological agent on and/or in the medical device is controllably released and some of the biological agent on the medical device is non-controllably released, or 3) none of the biological agent on and/or in the medical device is controllably released. The medical device can also be designed such that the rate of release of the one or more biological agents from the medical device is the same or different. The medical device can also be designed such that the rate of release of the one or more biological agents from one or more regions on the medical device is the same or different. Non-limiting arrangements that can be used to control the release of one or more biological agent from the medical device include a) at least partially coat one or more biological agents with one or more polymers, b) at least partially incorporate and/or at least partially encapsulate one or more biological agents into and/or with one or more polymers, and/or c) insert one or more biological agents in pores, passageway, cavities, etc. in the medical device and at least partially coat or cover such pores, passageway, cavities, etc. with one or more polymers. As can be appreciated, other or additional arrangements can be used to control the release of one or more biological agent from the medical device. The one or more polymers used to at least partially control the release of one or more biological agent from the medical device can be porous or non-porous. The one or more biological agents can be inserted into and/or applied to one or more surface structures and or micro-structures on the medical device, and/or be used to at least partially form one or more surface structures and/or micro-structures on the medical device. As such, the one or more biological agents on the medical device can be 1) coated on one or more surface regions of the medical device, 2) inserted and/or impregnated in one or more surface structures and/or micro-structures, etc. of the medical device, and/or 3) form at least a portion or be included in at least a portion of the structure of the medical device. When the one or more biological agents are coated on the medical device, the one or more biological agents can 1) be directly coated on one or more surfaces of the medical device, 2) be mixed with one or more coating polymers or other coating materials and then at least partially coated on one or more surfaces of the medical device, 3) be at least partially coated on the surface of another coating material that has been at least partially coated on the medical device, and/or 4) be at least partially encapsulated between a) a surface or region of the medical device and one or more other coating materials and/or b) two or more other coating materials. As can be appreciated, many other coating arrangements can be additionally or alternatively used. When the one or more biological agents are inserted and/or impregnated in one or more surface structures and/or micro-structures of the medical device, 1) one or more other coating materials can be applied at least partially over the one or more surface structures and/or micro-structures of the medical device, and/or 2) one or more polymers can be combined with one or more biological agents. As can be appreciated, many other and/or additional coating combinations and/or configurations can be used. The concentration of one or more biological agents, the type of polymer, and/or the coating thickness of one or more biological agents can be used to control the release time, the release rate and/or the dosage amount of one or more biological agents; however, other or additional combinations can be used. As such, the biological agent and polymer system combination and location on the medical device can be numerous. As can also be appreciated, one or more biological agents can be deposited on the top surface of the medical device to provide an initial burst effect of the one or more biological agents prior to 1) the control release of the one or more biological agents through one or more layers of polymer system that include one or more non-porous polymers and/or 2) the uncontrolled release of the one or more biological agents through one or more layers of polymer system. The one or more biological agents and/or polymers can be coated on the medical device by a variety of mechanisms such as, but not limited to, spraying (e.g., atomizing spray techniques, etc.), dip coating, roll coating, sonication, brushing, plasma deposition, and/or depositing by vapor deposition. The thickness of each polymer layer and/or layer of biological agent is generally at least about $0.01\mu$ and is generally less than about $150\mu$. In one non-limiting embodiment, the thickness of a polymer layer and/or layer of biological agent is about $0.02$-$75\mu$, and more particularly about $0.05$-$50\mu$. When the medical device includes and/or is coated with one or more biological agents such that at least one of the biological agents is at least partially controllably released from the medical device, the need or use of body-wide therapy for extended periods of time can be reduced or eliminated. In the past, the use of body-wide therapy was used by the patient long after the patient left the hospital or other type of medical facility. This body-wide therapy could last days, weeks, months or sometimes over a year after surgery. The medical device of the present invention can be applied or inserted into a treatment area and 1) merely requires reduced use and/or extended use of body wide therapy after application or insertion of the medical device or 2) does not require use and/or extended use of body wide therapy after application or insertion of the medical device. As can be appreciated, use and/or extended use of body wide therapy can be used after application or insertion of the medical device at the treatment area. In one non-limiting example, no body-wide therapy is needed after the insertion of the medical device into a patient. In another non-limiting example, short term use of body-wide therapy is needed or used after the insertion of the medical device into a patient. Such short term use can be terminated after the release of the patient from the hospital or other type of medical facility, or one to two days or weeks after the release of the patient from the hospital or other type of medical facility; however, it will be appreciated that other time periods of body-wide therapy can be used. As a result of the use of the medical device of the present invention, the use of body-wide therapy after a medical procedure involving the insertion of a medical device into a treatment area can be significantly reduced or eliminated.

In another and/or alternative non-limiting aspect of the present invention, controlled release of one or more biological agents from the medical device, when controlled release is desired, can be accomplished by using one or more non-porous polymer layers; however, other and/or additional mechanisms can be used to controllably release the one or more biological agents. The one or more biological agents are at least partially controllably released by molecular diffusion through the one or more non-porous polymer layers. When one or more non-porous polymer layers are used, the one or more polymer layers are typically biocompatible polymers; however, this is not required. The one or more non-porous polymers can be applied to the medical device without the use of chemical, solvents, and/or catalysts; however, this is not required. In one non-limiting example, the non-porous polymer can be at least partially applied by, but not limited to, vapor deposition and/or plasma deposition. The non-porous polymer can be selected so as to polymerize and cure merely upon condensation from the vapor phase; however, this is not required. The application of the one or more non-porous polymer layers can be accomplished without increasing the temperature above ambient temperature (e.g., 65-90° F.); however, this is not required. The non-porous polymer system can be mixed with one or more biological agents prior to being coated on the medical device and/or be coated on a medical device that previously included one or more biological agents; however, this is not required. The use or one or more non-porous polymer layers allow for accurate controlled release of the biological agent from the medical device. The controlled release of one or more biological agents through the non-porous polymer is at least partially controlled on a molecular level utilizing the motility of diffusion of the biological agent through the non-porous polymer. In one non-limiting example, the one or more non-porous polymer layers can include, but are not limited to, polyamide, parylene (e.g., parylene C, parylene N) and/or a parylene derivative.

In still another and/or alternative non-limiting aspect of the present invention, controlled release of one or more biological agents from the medical device, when controlled release is desired, can be accomplished by using one or more polymers that form a chemical bond with one or more biological agents.

In one non-limiting example, at least one biological agent includes trapidil, trapidil derivative or a salt thereof that is covalently bonded to at least one polymer such as, but not limited to, an ethylene-acrylic acid copolymer. The ethylene is the hydrophobic group and acrylic acid is the hydrophilic group. The mole ratio of the ethylene to the acrylic acid in the copolymer can be used to control the hydrophobicity of the copolymer. The degree of hydrophobicity of one or more polymers can be also be used to control the release rate of one or more biological agents from the one or more polymers. The amount of biological agent that can be loaded with one or more polymers may be a function of the concentration of anionic groups and/or cationic groups in the one or more polymer. For biological agents that are anionic, the concentration of biological agent that can be loaded on the one or more polymers is generally a function of the concentration of cationic groups (e.g. amine groups and the like) in the one or more polymer and the fraction of these cationic groups that can ionically bind to the anionic form of the one or more biological agents. For biological agents that are cationic (e.g., trapidil, etc.), the concentration of biological agent that can be loaded on the one or more polymers is generally a function of the concentration of anionic groups (i.e., carboxylate groups, phosphate groups, sulfate groups, and/or other organic anionic groups) in the one or more polymers, and the fraction of these anionic groups that can ionically bind to the cationic form of the one or more biological agents. As such, the concentration of one or more biological agent that can be bound to the one or more polymers can be varied by controlling the amount of hydrophobic and hydrophilic monomer in the one or more polymers, by controlling the efficiency of salt formation between the biological agent, and/or the anionic/cationic groups in the one or more polymers.

In still another and/or alternative non-limiting aspect of the present invention, controlled release of one or more biological agents from the medical device, when controlled release is desired, can be accomplished by using one or more polymers that include one or more induced cross-links. These one or more cross-links can be used to at least partially control the rate of release of the one or more biological agents from the one or more polymers. The cross-linking in the one or more polymers can be instituted by a number to techniques such as, but not limited to, using catalysts, using radiation, using heat, and/or the like. The one or more cross-links formed in the one or more polymers can result in the one or more biological agents to become partially or fully entrapped within the cross-linking, and/or form a bond with the cross-linking. As such, the partially or fully biological agent takes longer to release itself from the cross-linking, thereby delaying the release rate of the one or more biological agents from the one or more polymers. Consequently, the amount of biological agent, and/or the rate at which the biological agent is released from the medical device over time can be at least partially controlled by the amount or degree of cross-linking in the one or more polymers.

In still a further and/or alternative aspect of the present invention, a variety of polymers can be coated on the medical device and/or be used to form at least a portion of the medical device. The one or more polymers can be used on the medical for a variety of reasons such as, but not limited to, 1) forming a portion of the medical device, 2) improving a physical property of the medical device (e.g., improve strength, improve durability, improve biocapatability, reduce friction, etc.), 3) forming a protective coating on one or more surface structures on the medical device, 4) at least partially forming one or more surface structures on the medical device, and/or 5) at least partially controlling a release rate of one or more biological agents from the medical device. As can be appreciated, the one or more polymers can have other or additional uses on the medical device. The one or more polymers can be porous, non-porous, biostable, biodegradable (i.e., dissolves, degrades, is absorbed, or any combination thereof in the body), and/or biocompatible. When the medical device is coated with one or more polymers, the polymer can include 1) one or more coatings of non-porous polymers; 2) one or more coatings of a combination of one or more porous polymers and one or more non-porous polymers; 3) one or more coatings of one or more porous polymers and one or more coatings of one or more non-porous polymers; 4) one or more coating of porous polymer, or 5) one or more combinations of options 1, 2, 3 and 4. The thickness of one or more of the polymer layers can be the same or different. When one or more layers of polymer are coated onto at least a portion of the medical device, the one or more coatings can be applied by a variety of techniques such as, but not limited to, vapor deposition and/or plasma deposition, spraying, dip-coating, roll coating, sonication, atomization, brushing and/or the like; however, other or additional coating techniques can be used. The one or more polymers that can be coated on the medical device and/or used to at least partially form the medical device can be polymers that considered to be biodegradable, bioresorbable, or bioerodable; polymers that are considered to be biostable; and/or polymers that can be made to be biodegradable and/or bioresorbable with modification. Non-limiting examples of polymers that considered to be biodegradable, bioresorbable, or bioerodable include, but are not limited to, aliphatic polyesters; poly(glycolic acid) and/or copolymers thereof (e.g., poly(glycolide trimethylene carbonate); poly(caprolactone glycolide)); poly(lactic acid) and/or isomers thereof (e.g., poly-L(lactic acid) and/or poly-D Lactic acid) and/or copolymers thereof (e.g. DL-PLA), with and without additives (e.g. calcium phosphate glass), and/or other copolymers (e.g. poly(caprolactone lactide), poly(lactide glycolide), poly(lactic acid ethylene glycol)); poly(ethylene glycol); poly(ethylene glycol) diacrylate; poly(lactide); polyalkylene succinate; polybutylene diglycolate; polyhydroxybutyrate (PHB); polyhydroxyvalerate (PHV); polyhydroxybutyrate/polyhydroxyvalerate copolymer (PHB/PHV); poly(hydroxybutyrate-co-valerate); polyhydroxyalkaoates (PHA); polycaprolactone; poly(caprolactone-polyethylene glycol) copolymer; poly(valerolactone); polyanhydrides; poly(orthoesters) and/or blends with polyanhydrides; poly(anhydride-co-imide); polycarbonates (aliphatic); poly(hydroxyl-esters); polydioxanone; polyanhydrides; polyanhydride esters; polycyanoacrylates; poly(alkyl 2-cyanoacrylates); poly(amino acids); poly(phosphazenes); poly(propylene fumarate); poly(propylene fumarate-co-ethylene glycol); poly(fumarate anhydrides); fibrinogen; fibrin; gelatin; cellulose and/or cellulose derivatives and/or cellulosic polymers (e.g., cellulose acetate, cellulose acetate butyrate, cellulose butyrate, cellulose ethers, cellulose nitrate, cellulose propionate, cellophane); chitosan and/or chitosan derivatives (e.g., chitosan NOCC, chitosan NOOC-G); alginate; polysaccharides; starch; amylase; collagen; polycarboxylic acids; poly(ethyl ester-co-carboxylate carbonate) (and/or other tyrosine derived polycarbonates); poly(iminocarbonate); poly(BPA-iminocarbonate); poly(trimethylene carbonate); poly(iminocarbonate-amide) copolymers and/or other pseudo-poly(amino acids); poly(ethylene glycol); poly(ethylene oxide); poly(ethylene oxide)/poly(butylene terephthalate) copolymer; poly(epsilon-caprolactone-dimethyltrimethylene carbonate); poly(ester amide); poly(amino acids) and conventional synthetic polymers thereof; poly(alkylene oxalates); poly(alkylcarbonate); poly(adipic anhydride); nylon copolyamides; NO-carboxymethyl chitosan NOCC); carboxymethyl cellulose; copoly(ether-esters) (e.g., PEO/PLA dextrans); polyketals; biodegradable polyethers; biodegradable polyesters; polydihydropyrans; poly-depsipeptides; polyarylates (L-tyrosine-derived) and/or free acid polyarylates; polyamides (e.g., Nylon 66, polycaprolactam); poly(propylene fumarate-co-ethylene glycol) (e.g., fumarate anhydrides); hyaluronates; poly-p-dioxanone; polypeptides and proteins; polyphosphoester; polyphosphoester urethane; polysaccharides; pseudo-poly(amino acids); starch; terpolymer; (copolymers of glycolide, lactide, or dimethyltrimethylene carbonate); rayon; rayon triacetate; latex; and/pr copolymers, blends, and/or composites of above. Non-limiting examples of polymers that considered to be biostable include, but are not limited to, parylene; parylene c; parylene f; parylene n; parylene derivatives; maleic anhydride polymers; phosphorylcholine; poly n-butyl methacrylate (PBMA); polyethylene-co-vinyl acetate (PEVA); PBMA/PEVA blend or copolymer; polytetrafluoroethene (Teflon®) and derivatives; poly-paraphenylene terephthalamide (Kevlar®); poly(ether ether ketone) (PEEK); poly(styrene-b-isobutylene-b-styrene) (Translute™); tetramethyldisiloxane (side chain or copolymer); polyimides polysulfides; poly(ethylene terephthalate); poly(methyl methacrylate); poly(ethylene-co-methyl methacrylate); styrene-ethylene/butylene-styrene block copolymers; ABS; SAN; acrylic polymers and/or copolymers (e.g., n-butyl-acrylate, n-butyl methacrylate, 2-ethylhexyl acrylate, lauryl-acrylate, 2-hydroxy-propyl acrylate, polyhydroxyethyl, methacrylate/methylmethacrylate copolymers); glycosaminoglycans; alkyd resins; elastin; polyether sulfones; epoxy resin; poly(oxymethylene); polyolefins; polymers of silicone; polymers of methane; polyisobutylene; ethylene-alphaolefin copolymers; polyethylene; polyacrylonitrile; fluorosilicones; poly(propylene oxide); polyvinyl aromatics (e.g. polystyrene); poly(vinyl ethers) (e.g. polyvinyl methyl ether); poly(vinyl ketones); poly(vinylidene halides) (e.g. polyvinylidene fluoride, polyvinylidene chloride); poly(vinylpyrolidone); poly(vinylpyrolidone)/vinyl acetate copolymer; polyvinylpridine prolastin or silk-elastin polymers (SELP); silicone; silicone rubber; polyurethanes (polycarbonate polyurethanes, silicone urethane polymer) (e.g., chronoflex varieties, bionate varieties); vinyl halide polymers and/or copolymers (e.g. polyvinyl chloride); polyacrylic acid; ethylene acrylic acid copolymer; ethylene vinyl acetate copolymer; polyvinyl alcohol; poly(hydroxyl alkylmethacrylate); Polyvinyl esters (e.g. polyvinyl acetate); and/or copolymers, blends, and/or composites of above. Non-limiting examples of polymers that can made to be biodegradable and/or bioresorbable with modification include, but are not limited to, hyaluronic acid (hyanluron); polycarbonates; polyorthocarbonates; copolymers of vinyl monomers; polyacetals; biodegradable polyurethanes; polyacrylamide; polyisocyanates; polyamide; and/or copolymers, blends, and/or composites of above. As can be appreciated, other and/or additional polymers and/or derivatives of one or more of the above listed polymers can be used. The one or more polymers can be coated on the medical device by a variety of mechanisms such as, but not limited to, spraying (e.g., atomizing spray techniques, etc.), dip coating, roll coating, sonication, brushing, plasma deposition, and/or depositing by vapor deposition. The thickness of each polymer layer is generally at least about 0.01µ and is generally less than about 150µ; however, other thicknesses can be used. In one non-limiting embodiment, the thickness of a polymer layer and/or layer of biological agent is about 0.02-75µ, and more particularly about 0.05-50µ. As can be appreciated, other thickness can be used. In one non-limiting embodiment, the medical device includes and/or is coated with parylene, PLGA, POE, PGA, PLLA, PAA, PEG, chitosan and/or derivatives of one or more of these polymers. In another and/or alternative non-limiting embodiment, the medical device includes and/or is coated with a non-porous polymer that includes, but is not limited to, polyamide, parylene c, parylene n and/or a parylene derivative. In still another and/or alternative non-limiting embodiment, the medical device includes and/or is coated with poly (ethylene oxide), poly(ethylene glycol), and poly(propylene oxide), polymers of silicone, methane, tetrafluoroethylene (including TEFLON brand polymers), tetramethyldisiloxane, and the like.

In another and/or alternative non-limiting aspect of the present invention, the medical device, when including and/or is coated with one or more biological agents, can include and/or can be coated with one or more biological agents that are the same or different in different regions of the medical device and/or have differing amounts and/or concentrations in differing regions of the medical device. For instance, the medical device can a) be coated with and/or include one or more biologicals on at least one portion of the body portion and at least another portion of the body portion is not coated with and/or includes biological agent; b) be coated with and/or include one or more biologicals on at least one portion of the body portion that is different from one or more biologicals on at least another portion of the body portion; c) be coated with and/or include one or more biologicals at a concentration on at least one portion of the body portion that is different from the concentration of one or more biologicals on at least another portion of the body portion; d) be coated with and/or include one or more biological agents on at least one portion of the flaring section and at least another portion of the flaring section is not coated with and/or includes biological agent; e) be coated with and/or include one or more biologicals on at least one portion of the flaring section that is different from one or more biologicals on at least another portion of the flaring section; f) be coated with and/or include one or more biological agents at a concentration on at least one portion of the flaring section that is different from the concentration of one or more biologicals on at least another portion of the flaring section; g) be coated with and/or include one or more biologicals on the body portion and the flaring section is not coated with and/or includes biological agent; h) be coated with and/or include one or more biologicals on the flaring section and the body portion is not coated with and/or includes biological agent; i) be coated with and/or include one or more biologicals on the body portion that is different from one or more biologicals on the flaring section; j) be coated with and/or include one or more biological agents at a concentration on the body portion that is different from the concentration of one or more biologicals on the flaring section; etc.

In still another and/or alternative non-limiting aspect of the present invention, one or more surfaces of the medical device can be treated to achieve the desired coating properties of the one or more biological agents and one or more polymers coated on the medical device. Such surface treatment techniques include, but are not limited to, cleaning, buffing, smoothing, etching (chemical etching, plasma etching, etc.), etc. When an etching process is used, various gasses can be used for such a surface treatment process such as, but not limited to, carbon dioxide, nitrogen, oxygen, Freon, helium, hydrogen, etc. The plasma etching process can be used to clean the surface of the medical device, change the surface properties of the medical device so as to affect the adhesion properties, lubricity properties, etc. of the surface of the medical device. As can be appreciated, other or additional surface treatment processes can be used prior to the coating of one or more biological agents and/or polymers on the surface of the medical device. In one non-limiting manufacturing process, one or more portions of the medical device are cleaned and/or plasma etched; however, this is not required. Plasma etching can be used to clean the surface of the medical device, and/or to form one or more non-smooth surfaces on the medical device to facilitate in the adhesion of one or more coatings of biological agents and/or one or more coatings of polymer on the medical device. The gas for the plasma etching can include carbon dioxide and/or other gasses. Once one or more surface regions of the medical device have been treated, one or more coatings of polymer and/or biological agent can be applied to one or more regions of the medical device. For instance, 1) one or more layers of porous or non-porous polymer can be coated on an outer and/or inner surface of the medical device, 2) one or more layers of biological agent can be coated on an outer and/or inner surface of the medical device, or 3) one or more layers of porous or non-porous polymer that includes one or more biological agents can be coated on an outer and/or inner surface of the medical device. The one or more layers of biological agent can be applied to the medical device by a variety of techniques (e.g., dipping, rolling, brushing, spraying, particle atomization, etc.). One non-limiting coating technique is by an ultrasonic mist coating process wherein ultrasonic waves are used to break up the droplet of biological agent and form a mist of very fine droplets. These fine droplets have an average droplet diameter of about 0.1-3 microns. The fine droplet mist facilitates in the formation of a uniform coating thickness and can increase the coverage area on the medical device.

In still yet another and/or alternative non-limiting aspect of the present invention, the body portion and/or the flaring section of the medical device can 1) include the same or different biological agents, 2) include the same or different amount of one or more biological agents, 3) include the same or different polymer coatings, 4) include the same or different coating thicknesses of one or more polymer coatings, 5) have one or more of both sections controllably release and/or uncontrollably release one or more biological agents, and/or 6) have one or more portions of one section controllably release one or more biological agents and one or more portions of the other section uncontrollably release one or more biological agents. In one non-limiting example, the body portion and the flaring section of the medical device can both or individually include one or more biological agents. In another and/or alternative non-limiting example, one or more biological agents are be the same or different on the body portion and/or the flaring section of the medical device. In still another and/or alternative non-limiting example, the body portion and/or the flaring section of the medical device are designed such that the entire amount of biological agent on the body portion and/or the flaring section is controllably released. In yet another and/or alternative non-limiting example, the body portion and/or the flaring section of the medical device are designed such that some of the biological agent on the body portion and/or the flaring section is controllably released and some of the biological agent on the body portion and/or the flaring section medical device is non-controllably released. In yet another and/or alternative non-limiting example, the body portion and/or the flaring section of the medical device are designed such that none of the biological agent on the body portion and/or the flaring section is controllably released. In still yet another and/or alternative non-limiting example, the body portion and/or the flaring section of the medical device are designed such that the body portion and/or the flaring section are designed such that the rate of release of the one or more biological agents from the body portion and/or the flaring section is the same or different.

In yet another and/or alternative non-limiting aspect of the invention, the medical device can include a marker material that facilitates enabling the medical device to be properly positioned in a body passageway. The marker material is typically designed to be visible to electromagnetic waves (e.g., x-rays, microwaves, visible light, inferred waves, ultraviolet waves, etc.); sound waves (e.g., ultrasound waves, etc.); magnetic waves (e.g., MRI, etc.); and/or other types of electromagnetic waves (e.g., microwaves, visible light, inferred waves, ultraviolet waves, etc.). In one non-limiting embodiment, the marker material is visible to x-rays (i.e., radiopaque). The marker material can form all or a portion of the medical device and/or be coated on one or more portions (flaring portion and/or body portion; at ends of medical device; at or near transition of body portion and flaring section; etc.) of the medical device. The location of the marker material can be on one or multiple locations on the medical device. The size of the one or more regions that include the marker material can be the same or different. The marker material can be spaced at defined distances from one another so as to form ruler like markings on the medical device to facilitate in the positioning of the medical device in a body passageway. The marker material can be a rigid or flexible material. The marker material can be a biostable or biodegradable material. When the marker material is a rigid material, the marker material is typically formed of a metal material (e.g., metal band, metal plating, etc.); however, other or additional materials can be used. The metal which at least partially forms the medical device can function as a marker material; however, this is not required. When the marker material is a flexible material, the marker material typically is formed of one or more polymers that are marker materials in-of-themselves and/or include one or more metal powders and/or metal compounds. In one non-limiting embodiment, the flexible marker material includes one or more metal powders in combinations with parylene, PLGA, POE, PGA, PLLA, PAA, PEG, chitosan and/or derivatives of one or more of these polymers. In another and/or alternative non-limiting embodiment, the flexible marker material includes one or more metals and/or metal powders of aluminum, barium, bismuth, cobalt, copper, chromium, gold, iron, stainless steel, titanium, vanadium, nickel, zirconium, niobium, lead, molybdenum, platinum, yttrium, calcium, rare earth metals, rhenium, zinc, silver, depleted radioactive elements, tantalum and/or tungsten; and/or compounds thereof. The marker material can be coated with a polymer protective material; however, this is not required. When the marker material is coated with a polymer protective material, the polymer coating can be used to 1) at least partially insulate the marker material from body fluids, 2) facilitate in retaining the marker material on the medical device, 3) at least partially shielding the marker material from damage during a medical procedure and/or 4) provide a desired surface profile on the medical device. As can be appreciated, the polymer coating can have other or additional uses. The polymer protective coating can be a biostable polymer or a biodegradable polymer (e.g., degrades and/or is absorbed). The coating thickness of the protective coating polymer material, when used, is typically less than about 300 microns; however, other thickness can be used. In one non-limiting embodiment, the protective coating materials include parylene, PLGA, POE, PGA, PLLA, PAA, PEG, chitosan and/or derivatives of one or more of these polymers.

In still another and/or alternative aspect of the invention, the medical device can be an expandable device that can be expanded by use of another device (e.g., balloon, etc.) and/or is self expanding. The expandable medical device can be fabricated from a material that has no or substantially no shape memory characteristics or can be fabricated from a material having shape-memory characteristics.

In a further and/or alternative non-limiting aspect of the present invention, the medical device or one or more regions of the medical device can be constructed by use of one or more microelectromechanical manufacturing techniques (MEMS (e.g., micro-machining, laser micro-machining, laser micro-machining, micro-molding, etc.)); however, other or additional manufacturing techniques can be used. The medical device can include one or more surface structures (e.g., pore, channel, pit, rib, slot, notch, bump, teeth, well, hole, groove, etc.). These structures can be at least partially formed by MEMS (e.g., micro-machining, etc.) technology and/or other types of technology. The medical device can include one or more micro-structures (e.g., micro-needle, micro-pore, micro-cylinder, micro-cone, micro-pyramid, micro-tube, micro-parallelopiped, micro-prism, micro-hemisphere, teeth, rib, ridge, ratchet, hinge, zipper, zip-tie like structure, etc.) on the surface of the medical device. Non-limiting examples of structures that can be formed on the medical devices such as stents are illustrated in United States Patent Publication Nos. 2004/0093076 and 2004/0093077, which are incorporated herein by reference. Typically, the micro-structures, when formed, extend from or into the outer surface no more than about 400 microns, and more typically less than about 300 microns, and more typically about 15-250 microns; however, other sizes can be used. The micro-structures can be clustered together or disbursed throughout the surface of the medical device. Similar shaped and/or sized micro-structures and/or surface structures can be used, or different shaped and/or sized micro-structures can be used. When one or more surface structures and/or micro-structures are designed to extend from the surface of the medical device, the one or more surface structures and/or micro-structures can be formed in the extended position and/or be designed so as to extend from the medical device during and/or after deployment of the medical device in a treatment area. The micro-structures and/or surface structures can be designed to contain and/or be fluidly connected to a passageway, cavity, etc.; however, this is not required. The one or more surface structures and/or micro-structures can be used to engage and/or penetrate surrounding tissue or organs once the medical device has be position on and/or in a patient; however, this is not required. The one or more surface structures and/or micro-structures can be used to facilitate in forming maintaining a shape of a medical device (i.e., see devices in United States Patent Publication Nos. 2004/0093076 and 2004/0093077). The one or more surface structures and/or micro-structures can be at least partially formed by MEMS (e.g., micro-machining, laser micro-machining, micro-molding, etc.) technology; however, this is not required. In one non-limiting embodiment, the one or more surface structures and/or micro-structures can be at least partially formed of a biological agent and/or be formed of a polymer. One or more of the surface structures and/or micro-structures can include one or more internal passageways that can include one or more materials (e.g., biological agent, polymer, etc.); however, this is not required. The one or more surface structures and/or micro-structures can be formed by a variety of processes (e.g., machining, chemical modifications, chemical reactions, MEMS (e.g., micro-machining, etc.), etching, laser cutting, etc.). The one or more coatings and/or one or more surface structures and/or micro-structures of the medical device can be used for a variety of purposes such as, but not limited to, 1) increasing the bonding and/or adhesion of one or more biological agents, adhesives, marker materials and/or polymers to the medical device, 2) changing the appearance or surface characteristics of the medical device, and/or 3) controlling the release rate of one or more biological agents. The one or more micro-structures and/or surface structures can be biostable, biodegradable, bioabsorbable, etc. One or more regions of the medical device that are at least partially formed by microelectromechanical manufacturing techniques can be biostable, biodegradable, bioabsorbable, etc. The medical device or one or more regions of the medical device can be at least partially covered and/or filled with a protective material so to at least partially protect one or more regions of the medical device, and/or one or more micro-structures and/or surface structures on the medical device from damage. One or more regions of the medical device, and/or one or more micro-structures and/or surface structures on the medical device can be damaged when the medical device is 1) packaged and/or stored, 2) unpackaged, 3) connected to and/or other secured and/or placed on another medical device, 4) inserted into a treatment area, 5) handled by a user, and/or 6) form a barrier between one or more micro-structures and/or surface structures and fluids in the body passageway. As can be appreciated, the medical device can be damaged in other or additional ways. The protective material can be used to protect the medical device and one or more micro-structures and/or surface structures from such damage. The protective material can include one or more polymers previously identified above. The protective material can be 1) biostable and/or biodegradable and/or 2) porous and/or non-porous. In one non-limiting design, the polymer is at least partially biodegradable so as to at least partially exposed one or more micro-structure and/or surface structure to the environment after the medical device has been at least partially inserted into a treatment area. In another and/or additional non-limiting design, the protective material includes, but is not limited to, sugar (e.g., glucose, fructose, sucrose, etc.), carbohydrate compound, salt (e.g., NaCl, etc.), parylene, PLGA, POE, PGA, PLLA, PAA, PEG, chitosan and/or derivatives of one or more of these materials; however, other and/or additional materials can be used. In still another and/or additional non-limiting design, the thickness of the protective material is generally less than about 300 microns, and typically less than about 150 microns; however, other thicknesses can be used. The protective material can be coated be one or more mechanism previously described herein.

In one non-limiting application, the medical device can be designed to be positioned within a vascular structure. The medical device can include a proximal and distal end, and have a certain diameter at the proximal end, and have a different diameter at the distal end, with multiple different diameters possible between the two ends. The medical device can have an expanded body portion with substantially the same diameter. The medical device can have an expanded body portion with multiple different diameters. The medical device can have one end that has the largest expanded diameter (i.e., the flaring section). The medical device can be designed to have a flaring section that can be expanded to a maximum flare angle of greater than 90°, yet enable the flaring section to be expanded in a body passageway such that at least one portion of the expanded flaring section is expanded to a flare angle of less than 90° and one or more other portions of the flaring section are expanded to a flare angle of greater than 90°. In one non-limiting design, the flaring section can be designed to enable the flare angle of the flaring section to be about 15-160°. The medical device can have the same or different architectural configurations for the body portion and the flaring section. The medical device can include a biostable and/or biodegradable material. The biostable material can be a shape memory material; however, this is not required. The biodegradable material, when used, can be dissolved, absorbed, degraded, or any combination thereof in the body. Various materials that can be used to form one or more portions of the medical device such as, but are not limited to, one or more metals and/or metal alloys (aluminum, barium, bismuth, brass, calcium, carbon, chromium, cobalt, cobalt-chromium alloy, copper, depleted radioactive elements, gold, iron, lead, magnesium, magnesium-zirconium alloy, magnesium-zinc alloy, molybdenum, molybdenum-rhenium alloy, nickel, Nitinol, niobium, platinum, rare earth metals, rhenium, silver, stainless steel, tantalum, tantalum-tungsten alloy, titanium, tungsten, vanadium, yttrium, zinc, zirconium, etc.), fiber materials (e.g., carbon fiber composites, fiberglass, etc.) and/or polymers (e.g., cellulose acetate, cellulose nitrate, silicone, polyethylene terephthalate, polyurethane, polyamide, polyester, polyorthoester, polyanhydride, polyether sulfone, polycarbonate, polypropylene, high molecular weight polyethylene, polytetrafluoroethylene, polylactic acid, polyglycolic acid or copolymers thereof, a polyanhydride, polycaprolactone, polyhydroxy-butyrate valerate or another biodegradable polymer or mixtures or copolymers of these, a protein, an extracellular matrix component, collagen, POE (e.g., Translute™), PEVA, PBMA, PLGA, fibrin, polyethylene tetraphthlate (Dacron), expandable polytetrafluoroethylene (e.g., Gortex, Impra, etc.), polyurethane, etc.). The medical device can be introduced into the vascular structure in a baseline form that is not its final form. The medical device can be balloon expandable; however, this is not required. The medical device can be self-expanding; however, this is not required. The medical device can be deployed by removing a physical hindrance to allow the medical device to at least partially assume its preformed baseline shape; however, this is not required. The physical hindrance can include, but is not limited to, an adhesive and/or sheath; however, other or additional physical hindrances can be used. The medical device can have on the surface and/or within the matrices of the medical device one or more layers of porous and/or non-porous polymer material; however, this is not required. The one or more polymer coatings can include biostable compounds and/or biodegradable compounds. The non-porous polymer material can allow for molecular diffusion of one or more biological agents through the non-porous polymer material; however, this is not required. The non-porous polymer material can include parylene and/or any derivative thereof, however, this is not required. Non-limiting examples of parylene include, but are not limited to, parylene C, parylene N or combinations thereof. The medical device can have on its surface and/or within the medical device one or more biological agents; however, this is not required. The biological agent can include, but is not limited to, includes trapidil, trapidil derivatives, taxol, taxol derivatives, cytochalasin, cytochalasin derivatives, paclitaxel, paclitaxel derivatives, rapamycin, rapamycin derivatives, 5-Phenylmethimazole, 5-Phenylmethimazole derivatives, GM-CSF, GM-CSF derivatives, or combinations thereof. It will be appreciated that other and/or additional biological agents can be used. The one or more biological agents can be coated on the medical device by a variety of techniques. The one or more biological agents can be at least partially covered and/or at least partially encapsulated by one or more polymer coatings on the medical device to at least partially control the release of the one or more biological agents from the medical device after the medical device has been inserted into a body passageway; however, this is not required. The thickness of the one or more polymer coatings can be selected and/or varied to at least partially control the rate of release of the one or more biological agents; however, this is not required. The medical device can include one or more regions that include porous sections and/or channels that can be used to at least partially contain one or more biological agents; however, this is not required. These porous sections and/or channels can be at least partially loaded with one or more biological agents and/or adhesive material prior to the application of one or more coatings of the polymer material of the medical device; however, this is not required. As can be appreciated, the medical device can be nano/micro structured to at least partially create the one or more porous sections and/or channels in the medical device; however, this is not required. The medical device can be formed by a variety of techniques such as, but not limited to, laser cutting, molding, MEMS (e.g., micro-machining) technology, and/or etching. The medical device can be at least partially formed of a biodegradable material and/or a non-biodegradable material. The medical device can be formed by one or more materials that have been mixed with one or more biological agents; however, this is not required. When the medical device is at least partially formed of a biodegradable polymer, the rate of release of the one or more biological agents, when one or more biological agents are used, from the medical device can be at least partially controlled by varying the concentrations of the one or more polymers and one or more biological agents used to form the medical device; however, this is not required.

It is one non-limiting object of the invention to provide for a medical device for the treatment of stenosis at the ostium of tubular organs.

It is another and/or alternative non-limiting object of the invention to provide for a medical device for the treatment of stenosis at the ostium of blood vessels.

It is still another and/or alternative non-limiting object of the invention to provide for a medical device which permits the stent to be firmly positioned at the ostium of tubular organs.

It is yet another and/or alternative non-limiting object of the present invention to provide a medical device which comprises a contoured expandable flange to permit the accurate positioning of the medical device, while at the same time preventing dislodgement of the medical device from the position where it had been placed.

It is still yet another and/or alternative non-limiting object of the present invention to provide a medical device which comprises a contoured expandable flange that provides improved coverage of the ostium.

It is a further and/or alternative non-limiting object of the present invention to provide a medical device which comprises a contoured expandable flange that crushes outwardly when contacted by an adjacent medical device.

Another and/or alternative non-limiting object of the present invention is the provision of a medical device that includes one or more surface structures and/or micro-structures.

Yet another and/or alternative non-limiting object of the present invention is the provision of a medical device that includes one or more internal structures, micro-structures and/or surface structures that include and/or are coated with one or more biological agents and/or polymers.

Still another and/or alternative non-limiting object of the present invention is the provision of a medical device that includes one or more surface structures, micro-structures and/ or internal structures and a protective coating that at least partially covers and/or protects such structures.

Yet another and/or alternative non-limiting object of the present invention is the provision of a medical device that includes one or more markers.

Still yet another and/or alternative non-limiting object of the present invention is the provision of a medical device that includes and/or is used with one or more physical hindrances.

These and other objects and advantages will become apparent from the following description taken together with the accompanying drawings.

BRIEF DESCRIPTION OF THE DRAWINGS

Reference may now be made to the drawings, which illustrate an embodiment that the invention may take in physical form and in certain parts and arrangements of parts wherein;

FIG. 1 illustrates a perspective view of one embodiment of the medical device in accordance with the invention showing the flared section at one end of the medical device;

FIG. 2 illustrates a sectional side view of the medical device of FIG. 1;

FIG. 3 illustrates and end view of the medical device of FIG. 1;

FIG. 4 illustrates the medical device that is collapsed and constrained within a retractable sheath type delivery device;

DETAILED DESCRIPTION OF THE INVENTION

Figure 5:
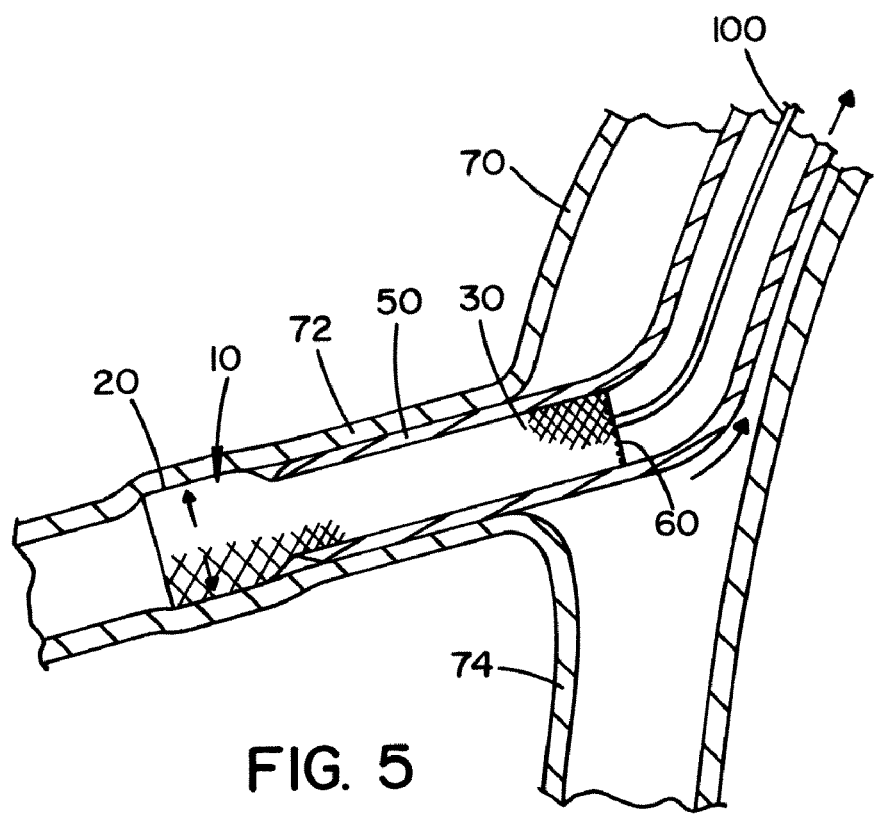
FIG. 5 illustrates the medical device and a delivery device positioned at the ostium of a vessel with the sheath about to be retracted.

Referring now to the drawings wherein the showings are for the purpose of illustrating the preferred embodiments only and not for the purpose of limiting the same, FIGS. 1-3 illustrate a medical device in an expanded state in accordance with the present invention. The medical device 10 includes an expandable body portion 20 and a flaring section 30. The body portion 20 has a generally uniform tubular shape along the longitudinal axis of the medical device; however, it will be appreciated that the body portion can have other shapes. The body portion is illustrated in FIG. 1 as having a generally constant diameter in the expanded state; however, this is not required. Typically, the body portion has a generally uniform tubular shape in the unexpanded state; however, this is not required. The flaring section 30 is shown to be in the expanded state as a diverging tubular shape or frustoconical shape. The transition between the body portion and the flaring section does not include any breaks. The structural pattern or configuration on the body portion (i.e., diamond shaped pattern) is illustrated as substantially the same as the structural pattern or configuration on the flaring section when both the body portion and flaring section are in the expanded state; however, this is not required. The diameter of the flaring section increases along the longitudinal length of the medical device. The maximum diameter of the flaring section in the expanded stated is at least about 25% greater than the minimum diameter of the body portion in the expanded state. The outer wall of the flaring section in the expanded state has a maximum flare angle relative to the longitudinal axis of the medical device that is over 90° as illustrated in FIGS. 1 and 2. Typically the flaring section in the expanded state has a maximum flare angle relative to the longitudinal axis of the medical device that is over 100°. Generally the maximum flare angle relative to the longitudinal axis of the medical device is less than about 160°; however, this is not required. The flare angle of the flaring section in the expanded state is illustrated as nonlinear along the longitudinal axis of the medical device. As such, the angle of flare of the flaring section increases from about 0° relative to a longitudinal axis of the medical device to a maximum flare angle at a nonlinear angular rate. The nonlinear angular rate can result from 1) a plurality of linear rates of flaring over the longitudinal length of the flaring section; 2) a continuously changing angle (e.g., curvilinear) over the longitudinal length of the flaring section as illustrated in FIGS. 1 and 2; or 3) a combination of one or more linear rates of flaring and one or more continuously changing angles over the longitudinal length of the flaring section.

FIGS. 1 and 2 illustrate that the flaring section and the body portion substantially transition into one another without having some type of spacing (e.g., interspace, etc.) between the body portion and the flaring section. As such, the stent configuration in accordance with the present invention is believed to be structurally superior to the stent disclosed in Mori U.S. Pat. No. 5,466,242. It is also believed that the stent configuration in accordance with the present invention has improved expansion properties as compared to the stent disclosed in Mori U.S. Pat. No. 5,466,242.

As illustrated in FIGS. 1 and 2, the flaring section has a smaller longitudinal length than the body portion. Generally, the body portion constitutes at least about 60 percent of the longitudinal length of the medical device; however, it can be appreciated that the body portion can constitute other percentages of the longitudinal length of the medical device. The flaring section and the body portion of the medical device are illustrated as formed from a plurality of intersecting wires or members. It can be appreciated that the flaring section and the body portion can be formed in a variety of ways, and is not limited to the plurality of intersecting wires or members as illustrated in FIGS. 1-3. As stated above, the structural pattern of the body portion and the flaring section is typically substantially the same; however, this is not required. As also illustrated in FIGS. 1-3, the flaring section maintains its single structure configuration even after being expanded. At least about 90-95% of the flaring section, in the expanded state, maintains a substantially single and uniform structure.

Prior to and during percutaneous insertion of the medical device into a tubular organ, the body portion and the flaring section in the unexpanded state have a generally uniform tubular shape as illustrated in FIG. 4; however, this is not required. Once the medical device has been delivered to the desired location in a tubular organ, the medical device is expanded and/or allowed to expand to its expanded state as illustrated in FIGS. 1-3. The geometric configuration of the walls of the medical device can vary for differing specific applications depending upon the requirements for rigidity, radial strength and flexibility. As illustrated in FIG. 3, a central passageway 40 exists along the longitudinal axis of the medical device. The diameter of the passageway when the medical device is in an expanded state is sufficient to allow various fluids (e.g., blood, etc.) to pass through the medical device when it has been set in a tubular organ.

Figure 6:
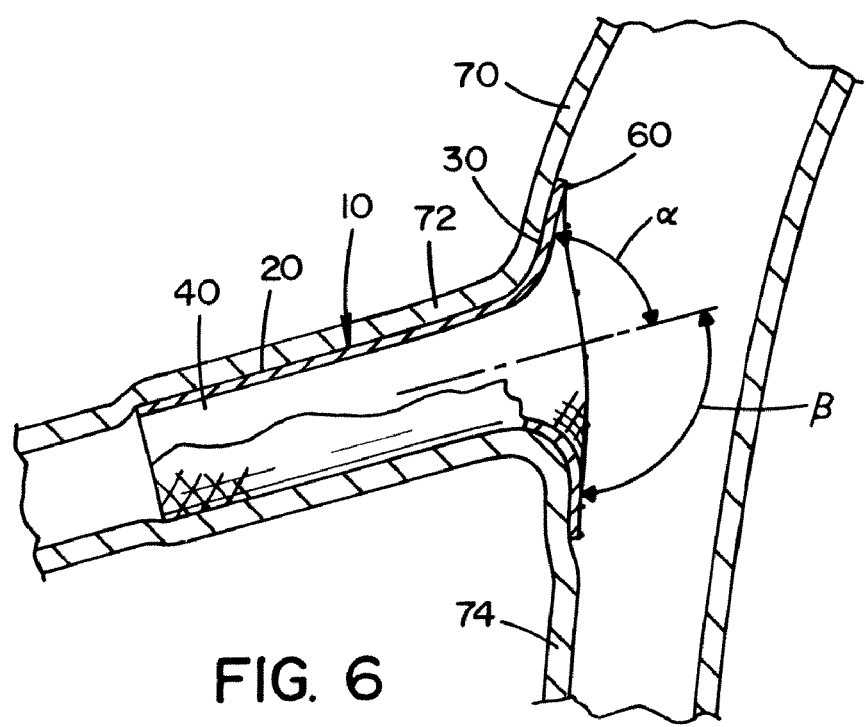
FIG. 6 illustrates the medical device in the fully extended position placed within the vessel and its ostium with the flared section of the medical device positioned against the wall of the originating organ.

Referring now to FIGS. 4-6, the medical device can be collapsed into its unexpanded state and be at least partially positioned in the vessel ostium by a delivery device. The medical device can include one or more markers such as radiopaque markers 60 at or near one or both ends of the medical device and/or at or near the location of the demarcation between the body portion and the flaring section so as to allow for better and more precise positioning of the medical device in a tubular organ. The medical device can be positioned in the vessel ostium using standard fluoroscopic and angiographic techniques. The medical device can be fabricated in different sizes to allow stenting of a wide variety of vessels or tubular passageways. Applications in which the medical device can be used include, but are not limited to, the ostial of the left main coronary artery, right coronary artery, innominate artery, left common carotid artery, subclavian artery, vertebral arteries, renal arteries, hepatic artery, and mesenteric arteries. Venous applications are also possible such as, but not limited to, the aorto-ostial anastomoses of saphenous vein grafts used in coronary artery bypass grafting.

In one non-limiting technique, the delivery device includes the use of a sheath 50 that can be retracted from the medical device to allow the medical device to expand to its expanded state. As shown in FIG. 4, medical device 10 is in the collapsed position or unexpanded state, constrained within the confines of retractable sheath 50. FIG. 5 illustrates the medical device in a retractable sheath delivery system inserted within a vessel 72 at its ostium with the sheath 50 of the delivery system being partially withdrawn after placement of the medical device 10. In one non-limiting example, vessel 70 can represent the left main (LM) coronary artery, vessel 72 can represent the left circumflex (LCx) coronary artery, and vessel 74 can represent the left anterior descending (LAD) coronary artery. As can be appreciated, the medical device can be inserted into other vessels or body passageways. As shown in FIG. 5, the medical device 10 is guided into the LCx by the delivery device. The delivery device is illustrated as including a guide rod 100 in combination with a sheath 50; however, it will be appreciated that other delivery systems could be used. Typically, the pre-expanded flaring section of the medical device sticks slightly out or protrudes in the LM and LAD prior to the expansion of the flaring section. When the flaring section is expanded, at least a portion of the flaring section expands over 90° to cover the wall about the LCx. As the sheath is removed, the uncovered portion of the medical device expands to its expanded state to facilitate in setting the medical device in the vessel. As can be appreciated, an angioplasty balloon, not shown, can be used to expand or facilitate in the expansion of the body portion and/or the flaring section.

Referring now to FIG. 6, sheath 50 is fully removed from the medical device and the medical device has fully expanded to its expanded state. The medical device is illustrated as firmly secured within vessel 72. The flaring section 30 of the medical device is illustrated as fully covering the ostium of vessel 72, which in this non-limiting example is the ostium of the LCx coronary artery. The flaring section is also illustrated as covering a portion of the LM coronary artery that encircles the ostium of the LCx coronary artery. Typically, the size of the flaring section is such that at least about 0.5 mm and typically up to about 3-4 mm of the LM coronary artery that encircles the ostium of the LCx coronary artery is covered by the flaring section of the stent. The flaring section of the stent is illustrated at conforming closely with the ostium and the region about the ostium. Because the maximum flare angle for the flaring section is greater than 90°, the outer lip of the flaring section can closely conform with the ostium and the region about the ostium. As illustrated in FIG. 6, flare angle α is less than 90° (e.g., 65°) and flare angle β is greater than 90° (e.g., 110°). Although the flaring section can be expanded to greater than 90°, the surface of LM coronary artery in one region about the ostium prevents further expansion of the flaring section in this region, thus a resulting flare angle of less than 90° at angle α is obtained after the flaring section has been fully expanded. In another region about the ostium, the surface of LAD coronary artery allows the flaring section to expand over 90° until the flaring section contacts the surface of the LAD coronary artery, thus a resulting flare angle of greater than 90° at angle β is obtained after the flaring section has been fully expanded.

The design of the flaring section of the medical device of the present invention is a significant improvement over prior art stents wherein 1) a significant portion of the ostium was not covered by the expanded prior art stent, 2) only a portion of the ostium was covered by the prior art stent, and/or 3) one or more portions of the stent formed a gap between the stent and a portion of the blood vessel. These limitations of prior stents are believed to result in an increased incidence of restenosis. In many prior art stents, more than 30 percent of the ostium would not be covered by use of the expanded prior art stent. In an effort to try and cover more of the ostium when using prior art stents, the proximal portion of the stent would be allowed to protrude further out into the parent vessel, in this case, the LM coronary artery. This increased protrusion is unacceptable as it may have adverse clinical consequences including, but not limited to, higher rates of subacute stent thrombosis. Increased protrusion into the parent vessel also increased the risk of inhibiting access to other branch vessels, in this case, the LAD coronary artery, for percutaneous intervention.

The flaring section of the medical device of the present invention is believed to overcome all these short comings of prior art stent. The flaring section of the medical device of the present invention is designed to cover at least about 85 percent of the ostium and up to 100% of the ostium in an expanded state without protruding too far into the parent vessel. As illustrated in FIG. 6, the flaring portion of the medical device minimizes or reduces the amount of the medical device that extends into the parent vessel 70, which is in this non-limiting example the LM coronary artery. The end portions of the flaring section engage or are closely adjacent to the surface of the LM coronary artery that surrounds the ostium. The flaring section 30 of the medical device in combination with a reduction in the amount of protrusion of the medical device into the parent vessel results in enough space to allow access to vessel 74, which is in this non-limiting example is the LAD coronary artery, for subsequent medical procedures if needed. The amount of protrusion of prior art stents into the parent vessel commonly resulted in impaired access to vessel 74, which impaired access could prevent the insertion of a stent into vessel 74 after a stent in vessel 72 has been deployed.

Referring now to FIG. 4, the expansion of the medical device can at least partially result from the inflation of a balloon and/or by use of shape memory materials to form the medical device. When a balloon 90 is used as illustrated in FIG. 4, the balloon is at least partially positioned in the unexpanded medical device. Once the medical device is properly positioned in a vessel, the balloon is expanded by a tube 100 to cause the medical device to at least partially expand to its expanded state. The balloon can be inflated prior to, during and/or after the sheath 50 has been at least partially removed from the medical device. After the balloon has at least partially expanded the medical device, the balloon is typically at least partially deflated and removed from the passageway of the medical device. As can be appreciated, the sheath and balloon delivery systems can be separate delivery systems that are used mutually exclusive on one another. As such the delivery system may only involve the use of a balloon or the use of a sheath.

Figure 7:
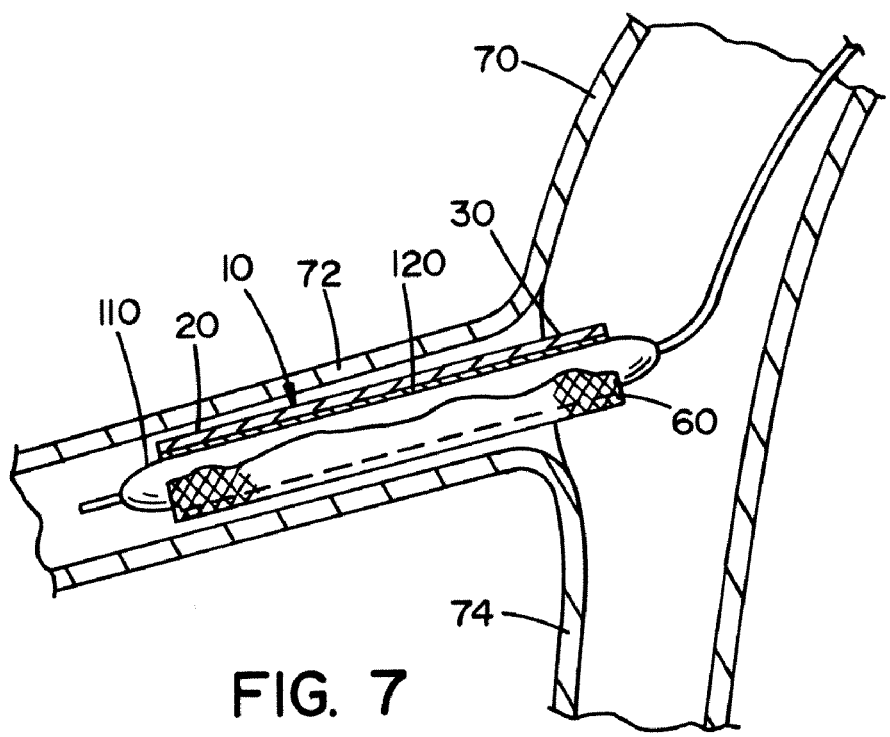
FIG. 7 illustrates the medical device and an alternative delivery device positioned at the ostium of a vessel.
Figure 8:
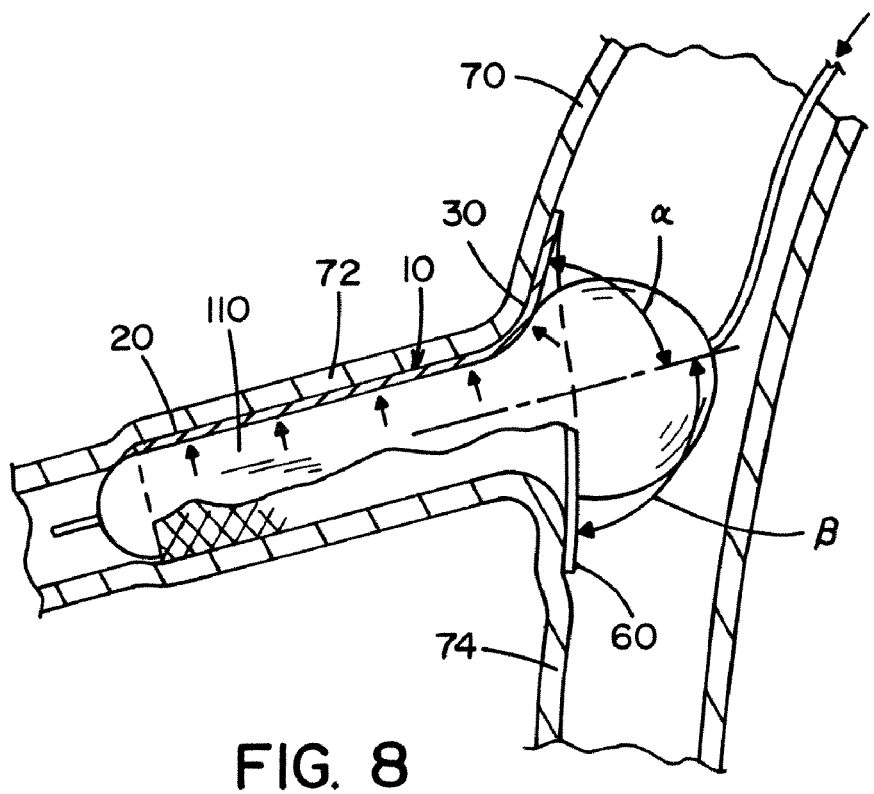
FIG. 8 illustrates the medical device and a delivery device positioned at the ostium of a vessel with a delivery device in an expanded state.

In another embodiment of the invention, an adhesive is used to at least partially secure the medical device to the balloon during the insertion of the medical device into a vessel as illustrated in FIGS. 7 and 8. In this embodiment, the delivery device includes a balloon 110 that is at least partially connected to the interior surface of the medical device 10 by an adhesive 120. As can be appreciated, the delivery device can also include a sheath that can be retracted from the medical device to allow the medical device to expand to its expanded state as illustrated in FIGS. 5 and 6. As shown in FIG. 7, medical device 10 is in the collapsed position or unexpanded state, constrained by the at least partially deflated balloon and adhesive 120. The collapsed medical device 10 is inserted into a vascular system by the delivery system and placed within vessel 72 at its ostia. In one non-limiting example, vessel 70 can represent the LM, vessel 72 can represent the LCx, and vessel 74 can represent the LAD. As can be appreciated, the medical device can be inserted into other vessels or body passageways. As shown in FIG. 7, the medical device 10 is guided into the LCx by the delivery device. Typically, the flaring section of the medical device sticks out in the LM prior to the expansion of the flaring section. As balloon 110 is inflated, the medical device expands to its expanded state to facilitate in setting the medical device in the vessel. The expansion of the balloon causes the adhesive between the balloon and the medical device to break down or otherwise release from the balloon and/or medical device; thereby at least partially releasing the medical device from the balloon. Once the medical device has been expanded, the balloon is at least partially deflated. Due to the break down or otherwise release from the balloon and/or medical device of the adhesive during the expansion of the medical device, the balloon can be removed from the medical device when the balloon is at least partially deflated without causing the medical device to be dislodged or be repositioned by the removal of the balloon from the medical device. As can be appreciated, some adhesive may be left on the balloon and/or medical device after the removal of the balloon. Typically the adhesive is a biocompatible material. The adhesive is typically a biodegradable material; however, this is not required. The adhesive can include one or more biological agents that can be used to provide localized dosages of such biological agents to the treated area. The one or more biological agents can be used to facilitate in the healing of the treated area, reduce pain in the treated area, reduce rejection of the medical device in the treated area, reduce restenosis and/or subacute thrombosis, reduce infection; and/or the like. The one or more biological agents in the adhesive can be controllably and/or uncontrollably released from the adhesive. The adhesive can be sprayed, painted, dipped, etc. on the medical device. One or more surfaces of the medical device can include the adhesive. The adhesive can be formulated to withstand sterilization of the medical device; however, this is not required.

Referring now to FIG. 8, the medical device has fully expanded to its expanded state. The medical device is illustrated as firmly secured within vessel 72. The flaring section 30 of the medical device is illustrated as fully covering the ostium of the LCx. The flaring section 30 is illustrated as encircling the ostium of the LCx coronary artery. Typically, the size of the flaring section is such that at least about 0.5 mm and typically up to about 3-4 mm of the LM coronary artery that encircles the ostium of the LCx coronary artery is covered by the flaring section of the stent. The flaring section of the stent is illustrated at conforming closely with the ostium and the region about the ostium. Because the maximum flare angle for the flaring section is greater than 90°, the outer lip of the flaring section can closely conform with the ostium and the region about the ostium. As illustrated in FIG. 8, flare angle α is less than 90° (e.g., 65°) and flare angle β is greater than 90° (e.g., 110°). Although the flaring section can be expanded to greater than 90°, the surface of LM coronary artery in one region about the ostium prevents further expansion of the flaring section in this region, thus a resulting flare angle of less than 90° at angle α is obtained after the flaring section has been fully expanded. In another region about the ostium, the surface of LM coronary artery allows the flaring section to expand over 90° until the flaring section contacts the surface of the LM coronary artery, thus a resulting flare angle of greater than 90° at angle β is obtained after the flaring section has been fully expanded. As previously stated, this design of the flaring section is a significant improvement over prior art stents.

The expansion of the medical device can at least partially result from the use of shape memory materials that are used to at least partially form the medical device. The use of shape memory materials can eliminate the use of a sheath and/or a balloon; however, it can be appreciated that the balloon and/or sheath can be used with medical devices that include shape memory materials.

The novel design of the medical device has many advantages over prior art stents. As stated above, the flaring section of the medical device increases the coverage of the ostium. The medical device is believed to reduce the incidence of restenosis. The flaring section of the medical device also simplifies the proper positioning of the medical device about the ostium. Prior stent designs required that the stent be positioned in a particular manner to achieve success of the stenting procedure. In most blood vessels, branching is not at a 90° angle. For instance the LCx may branch from the LM coronary artery at about a 40-130° angle, and thus the ostium of the LCx will not be at a right angle to the LM. To try to partially compensate for this angular orientation, one end of prior art stents was positioned such that the end partially extended or protruded from the ostium into the LM coronary artery; however, incomplete coverage of the ostium of the LCx still resulted. Prior art stents that included a uniform flaring section with an exact point on the stent where the uniform flaring began is illustrated in U.S. Pat. No. 5,466, 242. This prior art stent had to be exactly positioned at the ostium in such a manner that the exact point of the start of the uniform flaring section corresponded exactly with the ostium of the vascular structure. Such precise positioning was difficult to achieve angiographically. The medical device of the present invention requires less exact positioning of the graft as required by prior art stents, while at the same time providing complete coverage of the ostium as compared to prior art stents. The non-uniform angular flaring section forms a trumpet-shaped region that more closely conforms to the ostium and region about the ostium. Due to the nature of the outward flare, the distance the medical device of the present invention that protrudes or extends into the parent vessel, such as the LM coronary artery, is minimized. The reduced amount of protrusion is believed to reduce the risk of subacute stent thrombosis and further allow future vascular access into other branch vessels, such as, the LAD coronary artery.

Figure 9:
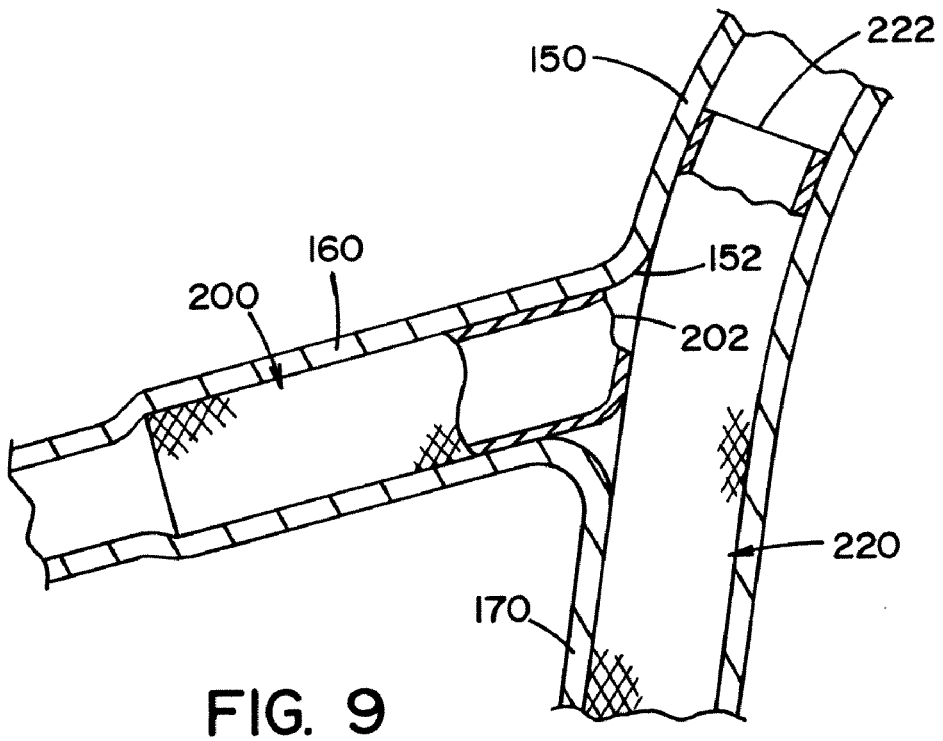
FIG. 9 illustrates a prior art stent procedure involving the use of two prior art stents at the ostium of a vessel; and, FIG. 10 illustrates a novel stent procedure in accordance with the present invention involving the use of the medical device of the present invention and another standard stent at the bifurcation of a vessel.

The novel design of the medical device of the present invention also reduces or eliminates the problems associated with the crushing of the end of the medical device by another stent. As illustrated in FIG. 9, a prior art stent 200 is positioned in vessel 150. In one non-limiting example, vessel 150 can represent the LM coronary artery, vessel 160 can represent the LCx coronary artery, and vessel 170 can represent the LAD coronary artery. As can be appreciated, the medical device can be inserted into other vessels or body passageways. Stent 200 is inserted into the LCx coronary artery and expanded by prior art techniques as described above to increase the flow of blood through the LCx coronary artery. One end 202 of the stent protrudes or sticks out from the ostium 152 of the LCx coronary artery into the LM coronary artery as done in standard practice. After stent 200 is positioned and expanded, a second stent 220 inserted from the LC coronary artery into the LAD to increase the flow of blood through this artery. If end 202 of stent 200 deployed in the LCx coronary artery protrudes too far into the LM coronary artery, the end of stent 200 could interfere with the proper deployment of stent 220 in the LM and LAD coronary arteries.

Assuming that stent 220 could be properly or at least partially deployed in the LM and LAD coronary arteries, the expansion of stent 220 commonly resulted in the body of stent 220 contacting end 202 of stent 200 and at least partially crushing end 202. The crushing of end 202 can result in reduced blood flow through the LCx, increase the amount of metal on metal contact at the ostium of the LCx coronary artery thereby 1) potentially increasing the risk of restenosis, 2) potentially increasing the risk of subacute thrombosis, and/or 3) potentially blocking future access into the LCx coronary artery via the LM coronary artery, which access may be required in the future to open the LCx downstream from the position of stent 200.

Figure 10:
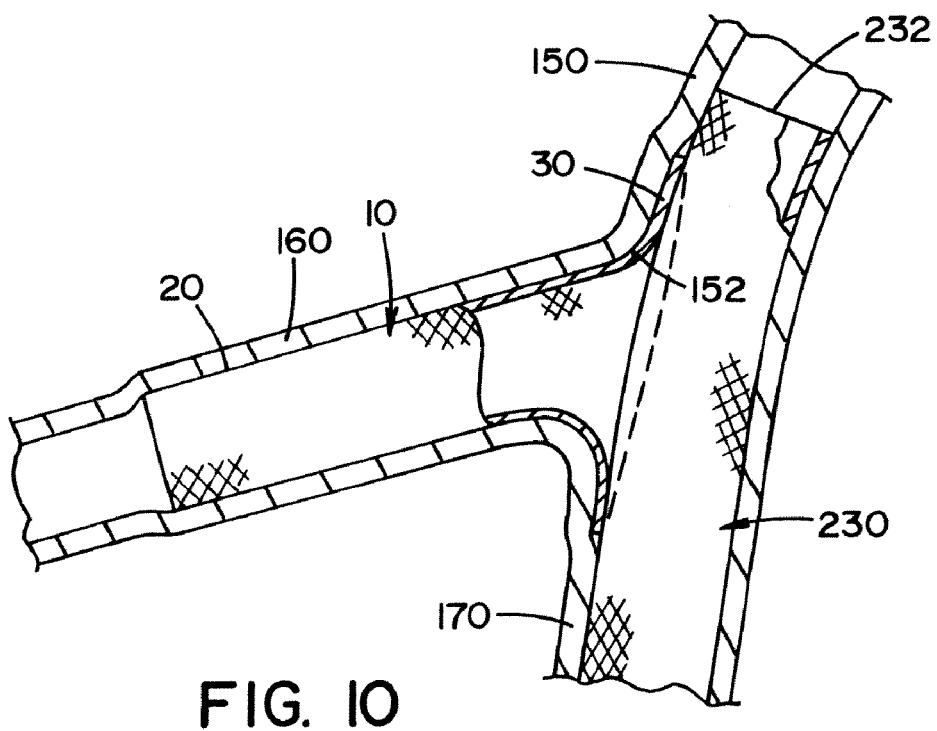

Referring now to FIG. 10, medical device 10 in accordance with the present invention is positioned in vessel 160. In one non-limiting example, vessel 150 can represent the LM coronary artery, vessel 160 can represent the LCx coronary artery, and vessel 170 can represent the LAD coronary artery. As can be appreciated, the medical device can be inserted into other vessels or body passageways. Medical device 10 is inserted into the LCx coronary artery and expanded by one or more of the techniques described above to increase the flow of blood through the LCx coronary artery. The flaring section 30 of the medical device fully covers the ostium 152 of the LCx coronary artery and conforms closely to the surface of the LM coronary artery about ostium 152. After medical device 10 is positioned and expanded, a second stent 230 is inserted into the LAD coronary artery from the LM coronary artery to increase the flow of blood through the LAD coronary artery. The expansion of stent 230 results in end 232 contacting a portion of flaring section 30 of medical device 10 and at least partially crushing flaring section 30. The crushing of flaring section 30 results in a portion of the flaring section being pushed further into the surface of the LM coronary artery about ostium 152. As a result of the outward flare of the medical device 10 of the present invention, which in this example has been positioned in the LCx coronary artery, the crushing of a portion of the flaring section is controlled such that the crushed portion of medical device 10 does not invaginate inwards to cover the ostium of the LCx coronary artery, but instead is crushed outwards against the walls of the LM coronary artery and the LAD coronary artery. As such, the crushing of the flaring section does not adversely affect the blood flow through the LCx coronary artery, retains complete coverage of ostium 152, and does not block future access into the LCx coronary artery via the LM coronary artery. The reduced amount of metal on metal contact resulting from the "controlled crush" of the flaring section of medical device 10 is believed to reduce the risk of restenosis and/or subacute thrombosis. This method of crushing of the flaring section of the medical device is a "controlled" crush. As such, the medical device of the present invention is particularly useful treating stenosis of the distal LM coronary artery, and/or the ostial LCX coronary artery, and/or the ostial LAD coronary artery; however, it will be appreciated that medical device can be used in other vessels or body passageways.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween.

We claim:

1. A method of stenting the ostium of a tubular organ comprising the steps of:
    a) inserting a medical device partially into said ostium, said medical device including a body portion and a flaring section, said body portion having a body diameter, said flaring section having a flaring diameter, said body diameter and said flaring diameter being different when said sections are in an expanded state, said flaring diameter being at least about 25% greater than a minimum body diameter of said body portion in an expanded state, said flaring section having a maximum flare angle in said expanded state that can be at least about 90° relative to a longitudinal axis of said body portion, said flaring section, and combinations thereof including one or more layers of porous material, non-porous material, and combinations thereof;
    b) expanding said medical device to cause said body portion to expand in at least a portion of said tubular organ and to cause said flaring section to substantially fully cover said ostium and to at least partially inhibit vasculature ingrowth in regions covered by said expanded flaring section, said flaring section in an expanded position substantially covering at least about 0.5 mm of a region about said ostium, at least a portion of said flaring section having a flare angle in said expanded state that is at least about 90° relative to a longitudinal axis of said body portion; and,
    c) at least partially controlling molecular diffusion of at least one biological agent through said layer of non-porous material.

2. The method as defined in claim 1, wherein at least a portion of said flaring section having a flare angle in said expanded state that is less than 90° relative to a longitudinal axis of said body portion.

3. The method as defined in claim 1, wherein said medical device includes a self-expanding body portion, a self-expanding flaring section, and combinations thereof.

4. The method as defined in claim 1, wherein medical device has a generally uniform structural pattern for said flaring section and said body portion in said expanded state.

5. The method as defined in claim 1, wherein said flaring section and said body portion are formed of the same material.

6. The method as defined in claim 1, wherein said body portion constitutes a majority of a longitudinal length of said medical device.

7. The method as defined in claim 1, wherein said flaring section has a nonlinear rate of flaring in said expanded state.

8. The method as defined in claim 1, wherein said non-porous material includes parylene or any derivative thereof.

9. The method as defined in claim 1, wherein said body portion, said flaring section, and combinations thereof includes at least one biological agent.

10. The method as defined in claim 9, wherein said biological agent includes trapidil, trapidil derivatives, GM-CSF, GM-CSF derivatives, and combinations thereof.

11. The method as defined in claim 1, including the step of at least partially expanding said medical device by a balloon.

12. The method as defined in claim 1, including the step of at least partially expanding said medical device by removing a physical hindrance on said medical device.

13. The method as defined in claim 12, wherein said physical hindrance includes an adhesive, a sheath, and combinations thereof.

14. The method as defined in claim 1, including the steps of inserting said medical device by use of a sheath type delivery system into the ostium of a tubular organ; and,
retracting the sheath to permit said medical device to at least partially expand to said expanded state.

15. The method as defined in claim 14, wherein a balloon is used to at least partially assist in the expansion of said medical device.

16. A method of stenting the ostium of a tubular organ comprising the steps of:
a) inserting a medical device by use of a sheath type delivery system partially into said ostium, said medical device including a body portion and a flaring section, said body portion having a body diameter, said flaring section having a flaring diameter, said body diameter and said flaring diameter being different when said sections are in an expanded state, said flaring diameter being at least about 25% greater than a minimum body diameter of said body portion in an expanded state, said flaring section formed of a substantially uniform and single structure in said expanded state, said flaring section having a maximum flare angle in said expanded state that is less than about 160° relative to a longitudinal axis of said body portion;
b) maintaining at least a portion of said medical device in an unexpanded state by use of an adhesive during insertion of said medical device in said vascular structure;
c) at least partially expanding said medical device to cause said body portion to expand in at least a portion of said tubular organ and to cause said flaring section to substantially fully cover said ostium and to at least partially inhibit vasculature ingrowth in regions covered by said expanded flaring section, said flaring section in an expanded position substantially covering at least about 0.5 mm of a region about said ostium, at least a portion of said flaring section having a flare angle in said expanded state that is less than about 160° relative to a longitudinal axis of said body portion, said step of at least partially expanding including the step of at least partially removing a physical hindrance on said medical device and inflating a balloon to at least partially cause said medical device to expand, said physical hindrance includes an adhesive, a sheath, and combinations thereof, said step of at least partially removing the physical hindrance including the step of at least partially retracting the sheath to permit said medical device to at least partially expand to said expanded state and at least partially breaking an adhesion by the adhesive between said balloon and said medical device by at least partially expanding said balloon.

17. The method as defined in claim 16, including the steps of inserting a second stent in the tubular organ and closely adjacent to said medical device after said medical device has been at least partially expanded, and expanding said second stent such that a portion of said second stent contacts at least a portion of said flaring section of said medical device and causes said portion of said flaring section to flare further outwardly.

18. The method as defined in claim 17, wherein said second stent is deployed extending from the left main coronary artery into said left anterior descending artery or said left circumflex artery.

19. The method as defined in claim 18, wherein said medical device is at east partially formed by MEMS technology.

20. The method as defined in claim 17, wherein said flaring section has a maximum flare angle in said expanded state that is at least about 90°.

21. The method as defined in claim 18, wherein said flaring section has a maximum flare angle in said expanded state that is at least about 90°.

22. The method as defined in claim 17, wherein body portion, said flaring section, and combinations thereof including one or more layers of porous material, non-porous material, and combinations thereof, and including the step of at least partially controlling molecular diffusion of at least one biological agent through said layer of non-porous material.

23. The method as defined in claim 21, wherein body portion, said flaring section, and combinations thereof including one or more layers of porous material, non-porous material, and combinations thereof, and including the step of at least partially controlling molecular diffusion of at least one biological agent through said layer of non-porous material.

* * * * *